United States Patent [19]

Schreiber et al.

[11] Patent Number: 5,447,915
[45] Date of Patent: Sep. 5, 1995

[54] TERMINALLY BLOCKED ANTIVIRAL PEPTIDES

[75] Inventors: Stuart Schreiber, Boston; Steven Burakoff, West Newton, both of Mass.

[73] Assignees: President and Fellows of Harvard College, Cambridge; Dana-Farber Cancer Institute, Inc., Boston, both of Mass.

[21] Appl. No.: 920,597

[22] PCT Filed: Feb. 21, 1991

[86] PCT No.: PCT/US91/01142

§ 371 Date: Aug. 28, 1992

§ 102(e) Date: Aug. 28, 1992

[87] PCT Pub. No.: WO91/13088

PCT Pub. Date: Sep. 5, 1991

Related U.S. Application Data

[63] Continuation-in-part of Ser. No. 486,522, Feb. 28, 1990, Pat. No. 5,115,098.

[51] Int. Cl.⁶ .................. A61K 37/02; G01N 33/566; G01N 33/569
[52] U.S. Cl. ........................ 514/18; 435/974; 436/63; 436/501; 514/2; 514/11; 514/19; 530/300; 530/317; 530/331; 548/537
[58] Field of Search ................ 436/63, 501; 435/974; 530/300, 317, 331, 335, 337, 345, 350, 868; 514/19, 423, 2, 11, 18; 548/530, 537, 538, 540

[56] References Cited

U.S. PATENT DOCUMENTS

| | | | |
|---|---|---|---|
| 3,705,887 | 12/1972 | Wieland et al. | 530/321 |
| 4,954,510 | 9/1990 | Tsuroka et al. | 514/315 |
| 5,023,338 | 6/1991 | Ocaln et al. | 548/336 |
| 5,091,366 | 2/1992 | Nutt et al. | 514/11 |
| 5,115,098 | 5/1992 | Burakoff et al. | 530/331 |
| 5,215,966 | 6/1993 | Hölzemann et al. | 514/19 |

FOREIGN PATENT DOCUMENTS 204374 12/1986 European Pat. Off.
04423 7/1986 WIPO.

OTHER PUBLICATIONS

Methoden Der Organischen Chemie (Houben-Weyl), published 1974, Band XV12, Synthese Von Peptiden Teil II, p. 328.

J. Med. Chemistry, vol. 11, issued 1968, Nicolaides et al, "Potential antiviral agents . . . ", pp. 74–79.

The Lancet, vol. 335, issued May 12, 1990, pp. 1128–1130.

Biochim, Biophys. Acta, vol. 989, issued 1989, Kieber–Emmons et al, "The gp120–CD4 interface . . . ", pp. 281–300.

Miller et al., 1968, Applied Microbiol. 16:1489–1496 (1968).

Mathur et al., 1982, Ind. J. Exp. Biol. 20:227–229 (1982).

Ringrose, 1983, Biochem. Soc. Trans. 11:804–808.

Konopinska et al., 1983, Int. J. Peptide Protein Res. 22:223–230.

Pert et al., 1986, Proc. Natl. Acad. Sci. USA 83:9254–9258.

(List continued on next page.)

*Primary Examiner*—Jeffrey E. Russel
*Attorney, Agent, or Firm*—Allegretti & Witcoff, Ltd.

[57] ABSTRACT

This invention relates to antiviral peptide compounds and to methods of inhibiting infection of human cells by viruses. This invention pertains more specifically to peptides that are chemically blocked at the amino- and carboxy-termini. In particular the invention relates to peptides comprised of prolylalanine or prolylphenylalanine compounds that have antiviral activity. The invention is specifically directed to methods for preventing infection of human cells in vivo and in vitro with the human immunodeficiency virus HIV-1 and methods for treating human infected with this and other viruses. The invention also relates to the diagnostic and therapeutic use of these antiviral peptide compounds.

23 Claims, 18 Drawing Sheets

CPF(LL)    X=OBn
CPF(C-Me)  X=OMe
CPF(+Leu)  X=NH-Leu-CO₂Bn

OTHER PUBLICATIONS

Dietrich et al., 1986, Int. J. Immunopharmac. 8:931–942.
Daher et al., 1986, J. Virol. 60:1068–1074.
Smith et al., 1987, Science 238:1704–1707.
Docherty et al., 1987, Antimicrob. Agents and Chemother. 31:1562–1566.
Fauci, 1988, Science 239:617–622.
Fisher et al, 1988, Nature 331:76–78.
Hussey et al., 1988, Nature 331:78–81.
Deen et al., 1988, Nature 331:82–84.
Traunecker et al, 1988, Nature 331:84–86.
Jameson et al., 1988, Science 240:1335–1339.
Lifson et al, 1988, Science 241:712–716.
Lobl et al., 1988, Int. J. Protein Res. 32:326–330.
Naruse et al., 1989, J. Antibiotics 42:837–845.
Nara et al., 1989, Proc. Natl. Acad. Sci. USA 86:7139–7143.
Bowman et al., 1990, Proc. Natl. Acad. Sci. USA 87:9052–9056.
Finberg et al., 1990, Science 249:287–291.
Srinivas et al., 1990, Virology 176:48–57.
Bjorck et al., 1990, J. Vir. 64:941–943.
Inocencio et al, 1990, Med. Microbiol. Immunol. 179:87–94.

CPF(LD)
CPF(DL) (ENANTIOMER OF CPF(LD))

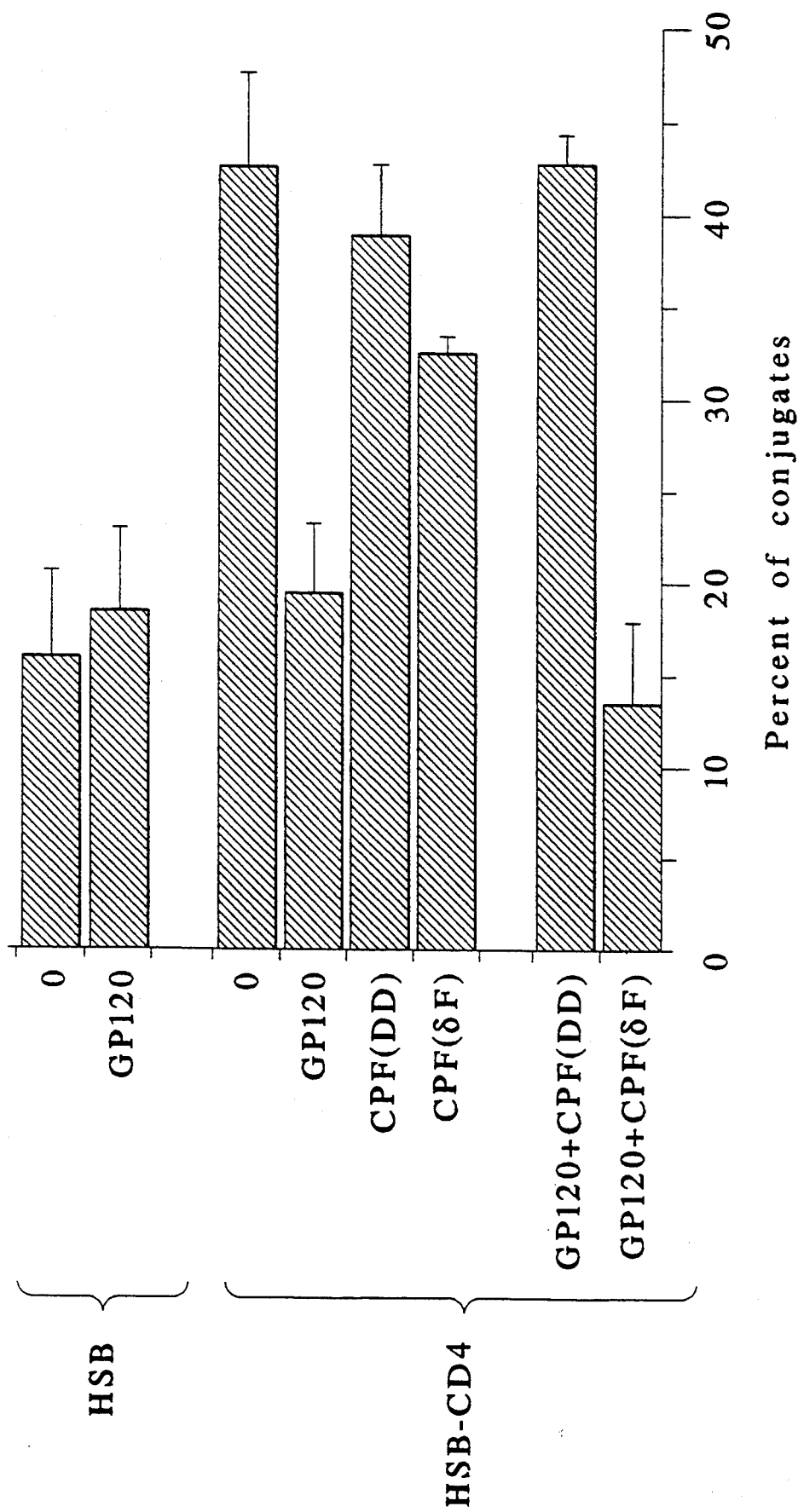

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Thr Lys Pro Lys Thr Lys Pro Lys
1               5
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Thr Lys Pro Lys Thr Lys Pro Arg
1               5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ala Lys Thr Lys Pro Arg Gln Gln
1               5
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ala  Ser  Thr  Thr  Thr  Asn  Tyr  Thr
1                 5
```

( 2 ) INFORMATION FOR SEQ ID NO:5:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Ala  Cys  Tyr  Cys  Arg  Ile  Pro  Ala  Cys  Ile  Ala  Gly  Glu  Arg  Arg  Tyr
1                 5                          10                         15

Gly  Thr  Cys  Ile  Tyr  Gln  Gly  Arg  Leu  Trp  Ala  Phe  Cys  Cys
              20                         25                    30
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Asp  Trp  Leu  Lys  Ala  Phe  Tyr  Asp  Lys  Val  Ala  Glu  Lys  Leu  Lys  Glu
1                 5                          10                         15

Ala  Phe
```

( 2 ) INFORMATION FOR SEQ ID NO:7:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Lys  Trp  Leu  Asp  Ala  Phe  Tyr  Lys  Asp  Val  Ala  Lys  Glu  Leu  Glu  Lys
1                 5                          10                         15

Ala  Phe
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Ile  Lys  Ile  Leu  Gly  Asn  Gln  Gly  Ser  Thr  Leu  Thr  Lys  Gly  Pro  Tyr
1                 5                          10                         15

Ser  Lys
```

( 2 ) INFORMATION FOR SEQ ID NO:9:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

```
Leu Lys Ile Glu Asp Ser Asp Thr Tyr Ile Cys Glu Val Glu Asp Gln
1               5                   10                  15
Lys Glu Glu
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Thr Tyr Ile Cys Glu Val Glu Asp Gln Lys Glu Glu
1               5                   10
```

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..5
        ( D ) OTHER INFORMATION: /label=Modifications
            / note="N-terminus blocked by
            N- carbomethoxycarbonyl or N-butoxycarbonyl;
            C-terminus blocked by methyl or benzyl ester; X ( i x ) FEATURE:
        ( A ) NAME/KEY: Peptide
        ( B ) LOCATION: 1..5
        ( D ) OTHER INFORMATION: /label=Variants
            / note="X residues at position 1 and 5 are any
            amino acid, and can vary from 0 residues to about
            100 residues at reach position;"

( x i ) SEQUENCE DESCRIPTION: SEQ ID NO:11:

```
Xaa Pro Xaa Leu Xaa
1               5
```

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY: Cross-links
        ( B ) LOCATION: 1..5
        ( D ) OTHER INFORMATION: /label=Cyclic
            / note="The amino and carboxyl termini are
            covalently linked;"

(ix) FEATURE:
    (A) NAME/KEY: Protein
    (B) LOCATION: 1..5
    (D) OTHER INFORMATION: /label=Variants
        / note="Position 1 and 5 X residue can be any amino acid from about 4 to about 100 residues, independently; position 3 X residue can be Ala, (xi) SEQUENCE DESCRIPTION: SEQ ID NO:12:

Xaa Pro Xaa Leu Xaa
1                 5

TERMINALLY BLOCKED ANTIVIRAL PEPTIDES

This invention was made with government support and the federal government has certain rights in the invention.

This is a continuation-in-part of U.S. Ser. No. 07/486,522, filed 28 Feb. 1990, now U.S. Pat. No. 5,115,098.

BACKGROUND OF THE INVENTION

1. Field of the Invention

This invention relates to antiviral peptide compounds and to methods of inhibiting infection of human cells by viruses. This invention pertains more specifically to peptides that are chemically blocked at the amino- and carboxy- termini. In particular the invention relates to peptides comprised of prolylalanine or prolylphenylalanine compounds that have antiviral activity. The invention is specifically directed to the inactivation of the human immunodeficiency virus and inhibition of infection of human cells in vivo and in vitro with this and other viruses. The invention also relates to the diagnostic and therapeutic use of these antiviral peptide compounds.

2. Background of the Related Art

The use of peptides having antiviral properties is known in the art. [See, Ringrose, Biochem. Soc. Trans. 11:804–808 (1983) for a review].

Miller et al., Applied Microbiol. 16: 1489–1496 (1967) describe the use of N-carbobenzoxy-derivatives of (D)-Phe-(D)-Phe, (L)-Phe-nitro-Arg, (D)-Phe-(D)-Phe-nitro-Arg, (D)-Phe-(D)-Met, (D)-Phe-Ala and (D)-Phe-S-benzyl-Cys to inhibit herpesvirus and measles virus infections in vivo and in vitro. These peptides were inactive against a wide variety of other viruses tested.

Mathur et al., Ind. J. Exp. Biol. 20:227–229 (1982) disclose the antiviral activity of poly($\alpha$-L-Lys) and poly($\epsilon$-L-Lys) against a number of double stranded RNA viruses in vivo, mediated by the induction of the antiviral protein interferon.

Konopinska et al., Int. J. Peptide Protein Res. 22: 223–230 (1983) disclose the antiviral activity of three tuftsin analogs (Thr-Lys-Pro-Lys-Thr-Lys-Pro-Lys, (Seq. ID. No.:1) Thr-Lys-Pro-Lys-Thr-Lys-Pro-Arg, (Seq. ID. No:2) and Ala-Lys-Thr-Lys-Pro-Arg-Gln-Gln) (Seq. ID. No:3) against murine sarcoma virus infection in vitro.

Pert et al., Proc. Natl. Acad. Sci. USA 83:9254–9258 (1986) disclose that the octapeptide Ala-Ser-Thr-Thr-Thr-Asn-Tyr-Thr (Seq. ID. No:4) displays antiviral activity against human immunodeficiency virus (HIV-1) in vitro.

Dietrich et al., Int. J. Immunopharmac. 8: 931–942 (1986) teach the use of N-acetyl-muramyl-(L)-alanyl-(D)-isoglutaryl-(L)-alanine-2-(1′,2′-dipalmitoyl-sn-glycero-3′hydroxyphosphoryloxy)ethylamide sodium salt for prophylactic treatment of animals to prevent infection by influenza virus types A and B, parainfluenza virus 1 and herpes simplex virus types 1 and 2. This compound had no antiviral effect in vitro, however.

Daher et al., J. Virol. 60: 1068–1074 (1986) disclose the discovery of a naturally-occurring peptide of sequence

```
Ala Cys Tyr Cys Arg Ile Pro Ala Cys Ile Ala Gly Glu Arg Arg Tyr
 1           5               10              15
Gly Thr Cys Ile Tyr Gln Gly Arg Leu Trp Ala Phe Cys Cys
          20              25              30    (SEQ ID No.: 5)
``` derived from human neutrophil cells that inhibits infection of human cells by herpes simplex virus 1 and 2, cytomegalovirus, vesicular stomatitis virus and influenza virus A in vitro.

Docherty et al., Antimicrob. Agents and Chemother. 31: 1562–1566 (1987) teach the use of synthetic polymers of histidine ($His_{24}$, $His_{64}$, and $His_{75}$) in vitro to effect the irreversible inhibition of infection of human cells with herpes simplex virus.

Lobl et al., Int. J. Protein Res. 32:326–330 (1988) teach the use of N-carbobenzoxy-(D)-Phe-Leu-Gly-(D)-Leu-(D)-Leu and N-carbobenzoxy-(D)-Phe-Leu-Gly-(D)-Leu-(D)-Leu-Gly to inhibit measles virus infection in vitro.

Naruse et al., J. Antibiotics 42:837–845 (1989) teach the use of a naturally-occurring peptide derived from *Streptoverticillium cinnamoneum* containing four unusual amino acids that displays antiviral activity against herpes simplex virus in vitro.

Srinivas et al., Virology 176:48–57 (1990) disclose the use of two synthetic peptides

```
Asp Trp Leu Lys Ala Phe Tyr Asp Lys Val Ala Glu Lys Leu Lys Glu
 1           5               10              15
Ala Phe (SEQ ID No.: 6)

Lys Trp Leu Asp Ala Phe Tyr Lys Asp Val Ala Lys Glu Leu Glu Lys
 1           5               10              15
Ala Phe (SEQ ID No.: 7)
``` homologous to a region of the human apolipoprotein A-1 sequence, to inhibit infection and viral spread of herpes simplex virus 1 in vitro.

BJorck et al., J. Vir. 64: 941–943 (1990) teach that the synthetic peptide N-benzoxycarbonyl-leucylvalylglycine diazomethylketone (Z-LVG-$CHN_2$) blocks the growth of herpes simplex virus but not poliovirus in vitro.

Inocencio et al., Med. Microbiol. Immunol. 179:87–94 (1990) disclose that the synthetic peptide Z-(D)-Phe-(L)-Phe displays antiviral activity against the paramyxoviruses rubeola, Sendal and Newcastle Disease virus in vitro.

Acquired immune deficiency syndrome (AIDS) is the most acute human public health problem to arise since the advent of the widespread use of antibiotics against bacterial infections over a generation ago. [See, Fauci, Science 239: 617–622 (1988) for a review]. The disease is widely believed to be caused by a virus, human immune deficiency virus 1 (HIV-1; also known as HTLV-III). The virus has been shown to enter human cells via its interaction with a specific cell surface receptor. This receptor, a glycoprotein termed CD4, is found on a specific class of human T lymphocytes that are the principle in vivo target for infection. This molecule is also a receptor for the Class II major histocompatibility complex (MHC) proteins that mediate immune recognition. Physiologically, CD4 is believed to bind a monomorphic domain on Class II MHC, thereby facilitating antigen recognition and enhancing T cell activation. Loss of this subset of T lymphocytes as a result of infection with HIV-1 results in the immune deficiency disorder. In addition, binding of CD4 by gp120 blocks the ability of CD4 to bind to Class II MHC or to be stimulated by Class II MHC, thereby interfering with effective immunological response to infection by HIV-1.

One approach to developing a method for preventing human infection with HIV-1 is to attempt to prevent binding between CD4 and HIV-1. Initial efforts involved the use of soluble forms of CD4, produced by expression of truncated forms of the protein by genetic engineering means. However, the use of the soluble forms of CD4 as therapeutic agents presents several problems in terms of delivery, stability and expense.

Smith et al., Science 238: 1704–1707 (1987) disclose the use of a soluble form of CD4, produced in CHO cells by expression and secretion of a truncated form of the protein directed by a transfected copy of a cDNA clone of the receptor gene, to inhibit HIV-1 infection of CD4+ human cells in vitro.

Fischer, et al., Nature 331:76–78 (1988) disclose the use of a soluble form of CD4, produced in CHO cells by expression and secretion of a truncated form of the protein directed by a transfected copy of a cDNA clone of the receptor gene, to inhibit HIV-1 infection of CD4+ human cells in vitro.

Hussey et al. Nature 331: 78–81 (1988) disclose the use of a soluble form of CD4, produced in insect cells transfected with a baculovirus vector containing a truncated CD4 cDNA, to inhibit HIV-1 infection of CD4+human cells in vitro.

Deen et al., Nature 331: 82–84 (1988) disclose the use of a soluble form of CD4, produced in CHO cells by expression and secretion of a truncated form of the protein directed by a transfected copy of a cDNA clone of the receptor gene, to inhibit HIV-1 infection of CD4+ human cells in vitro.

Traunecker et al., Nature 331: 84–86 (1988) disclose the use of a soluble form of CD4, produced in myeloma cells by expression and secretion of a truncated form of the protein directed by a transfected copy of a cDNA clone of the receptor gene, to inhibit HIV-1 infection of CD4+ human cells in vitro.

It is known that the envelope glycoprotein of the virus, gp120, binds to CD4 by way of specific binding sites present in both molecules that mediate their recognition. The respective binding sites of both glycoproteins have been mapped. Subsequent efforts have focused on the use of CD4-derived synthetic peptides to inhibit binding of CD4 to HIV-1 gp120.

Jameson et al., Science 240: 1335–1339 (1988) disclose the use of a synthetic peptide,

| Ile | Lys | Ile | Leu | Gly | Asn | Gln | Gly | Ser | Thr | Leu | Thr | Lys | Gly | Pro | Tyr |
|---|---|---|---|---|---|---|---|---|---|---|---|---|---|---|---|
| 1 | | | | 5 | | | | | 10 | | | | | 15 | |

Ser Lys (SEQ ID No.: 8)

derived from the deduced CD4-gp120 binding site by immunological studies, to bring about a decrease in HIV-1 induced cell fusion in vitro.

Lifson et al., Science 241:712–716 (1988) disclose the use of a mixture of the synthetic peptide

| Leu | Lys | Ile | Glu | Asp | Ser | Asp | Thr | Tyr | Ile | Cys | Glu | Val | Glu | Asp | Gln |
|---|---|---|---|---|---|---|---|---|---|---|---|---|---|---|---|
| 1 | | | | 5 | | | | | 10 | | | | | 15 | |

Lys Glu Glu (SEQ ID No. 9)

derived from CD4, and side products produced during the synthesis of this peptide, that inhibit HIV-1 infection and cytopathicity in vitro.

Nara et al., Proc. Natl. Acad. Sci. USA 86:7139–7143 (1989) teach the use of the synthetic peptide

| Thr | Tyr | Ile | Cys | Glu | Val | Glu | Asp | Gln | Lys | Glu | Glu | (SEQ ID No. 10) |
|---|---|---|---|---|---|---|---|---|---|---|---|---|
| 1 | | | | 5 | | | | | 10 | | | | derived from CD4, to inhibit HIV-1 infection in vitro.

Thus, as summarized herein, it was known in the prior art that peptides derived from epitopes of CD4 that had an inhibitory effect on HIV-1 infection also prevented the binding of epitope-specific anti-CD4 antibodies. It was also known in the art that the efficiency of inhibition of virus infection increased with the size of the peptide (Jameson et al., supra).

Bowman et al., Proc. Natl. Acad. Sci. USA 87:9052–9056 (1990) examined the binding interaction between CD4 and gp120 using epitope loss mutants, produced by genetic engineering means and expressed in otherwise CD4− cells in vitro, and found that a particular class of such mutants specifically resulted in loss of the ability to bind gp120. These mutants were unique in that they did not display any change in their ability to recognize epitope-specific anti-CD4 antibodies. This result indicated that the alteration in the gp120 binding ability of these mutants was not the result of dramatic changes in the conformation of the CD4 protein, and suggested that this particular epitope might specifically interact with gp120. Molecular modeling studies showed that this peptide had predominantly a β-sheet secondary structure, and that in this structure the side-chain of $Phe^{43}$ would conspicuously protrude from the surface of the protein.

Finberg et al., Science 249: 287–291 (1990) designed and tested a number of amino- and carboxy-terminally blocked di- and tri-peptides for their ability to inhibit binding of HIV-1 gp120 to CD4 expressed on HBS cells. Some of the peptides tested displayed the inhibitory activity and are among those comprehended by the present invention. Antiviral peptides according to the present invention are unique in that these peptides specifically bind to gp120 rather than to CD4.

BRIEF DESCRIPTION OF THE DRAWINGS

FIG. 6 illustrates the ability of incubation with the peptides of the invention to overcome HIV-1 gp120 mediated inhibition of conjugate formation between CD4+ cells and MHC-expressing cells in vicro.

SUMMARY OF THE INVENTION

Figure 1A:
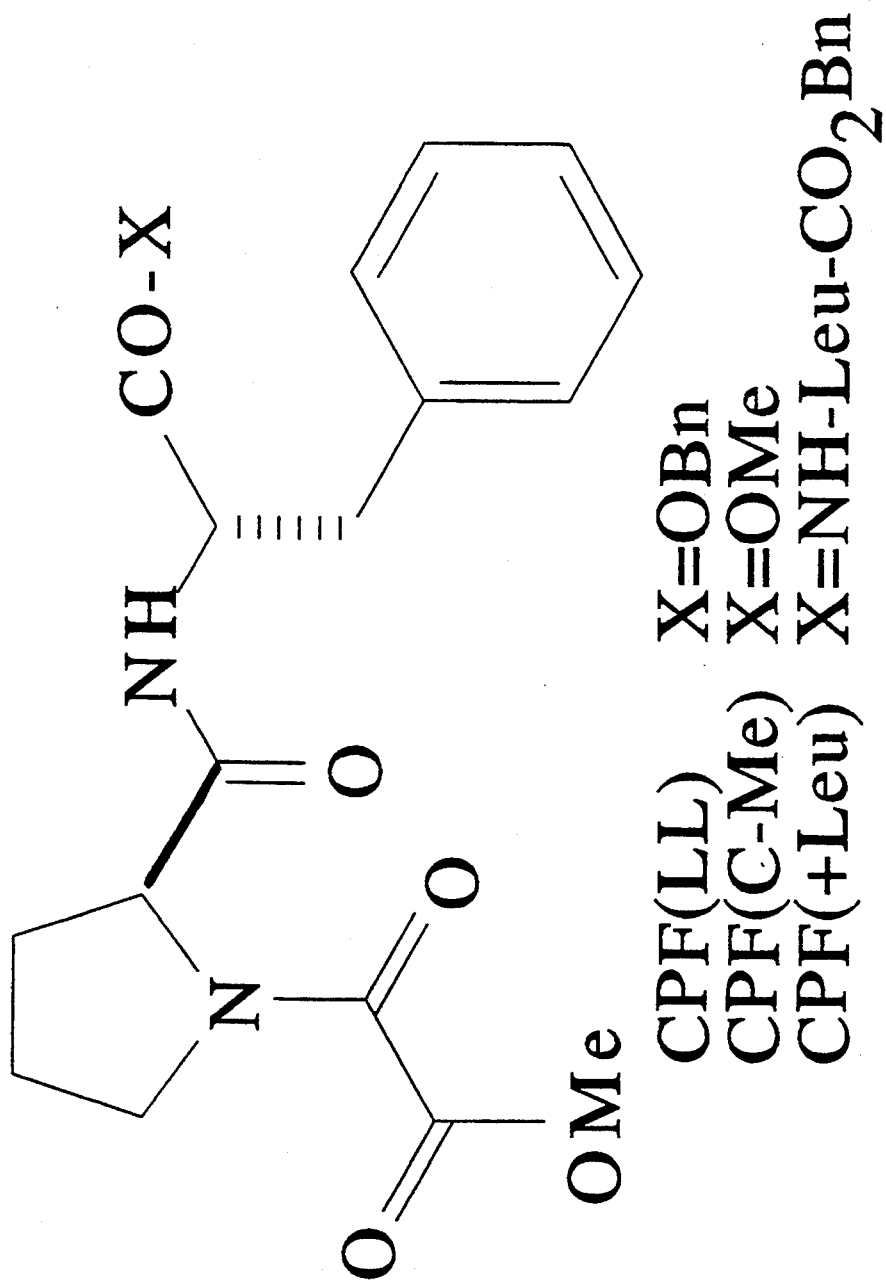
FIG. 1A through 1G illustrates the structures of the peptides of the invention.
Figure 1B:
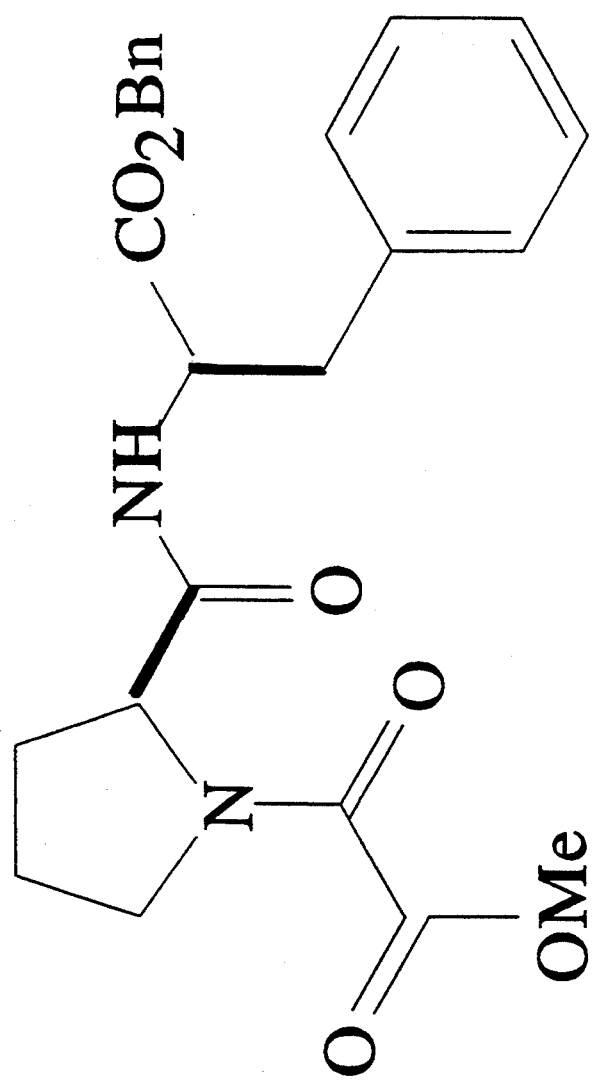
Figure 1C:
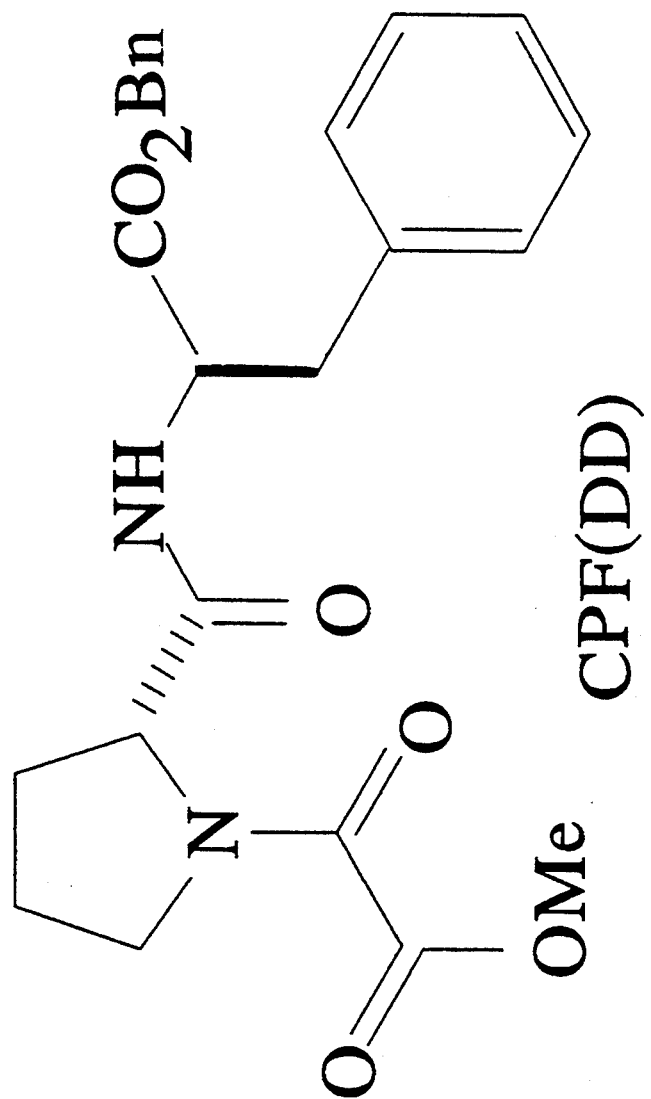
Figure 1D:
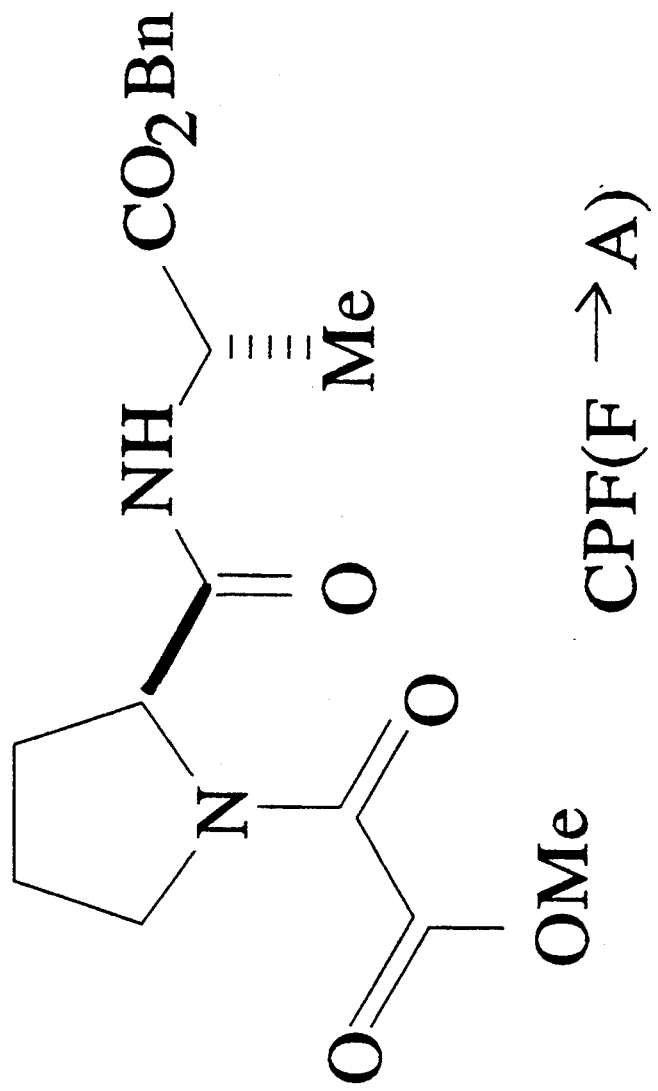
Figure 1E:
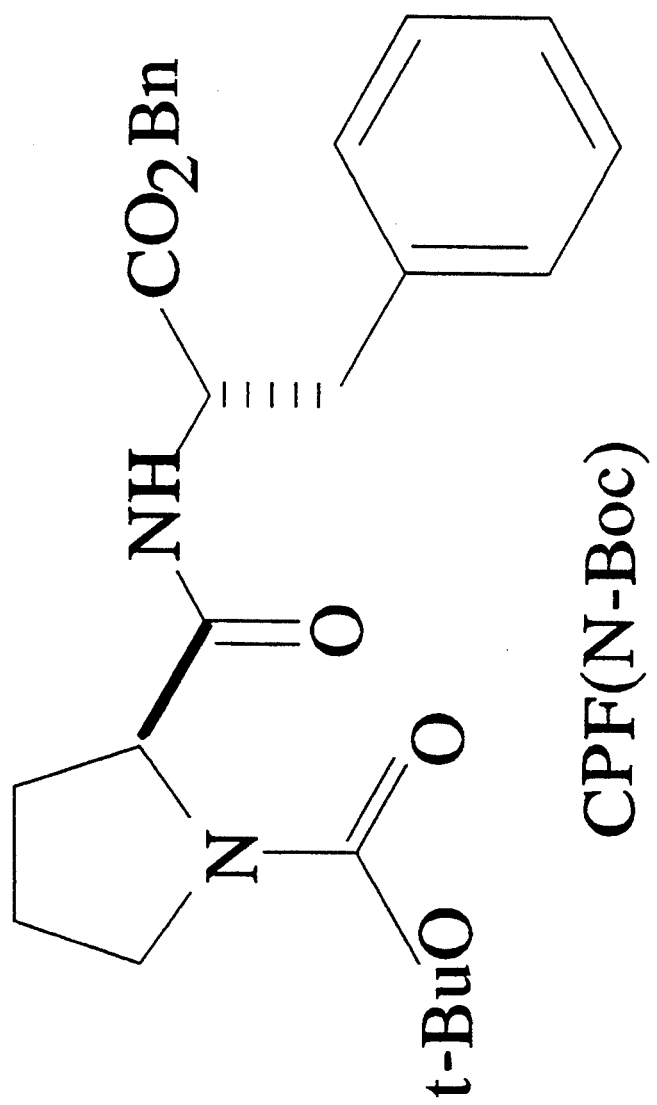
Figure 1F:
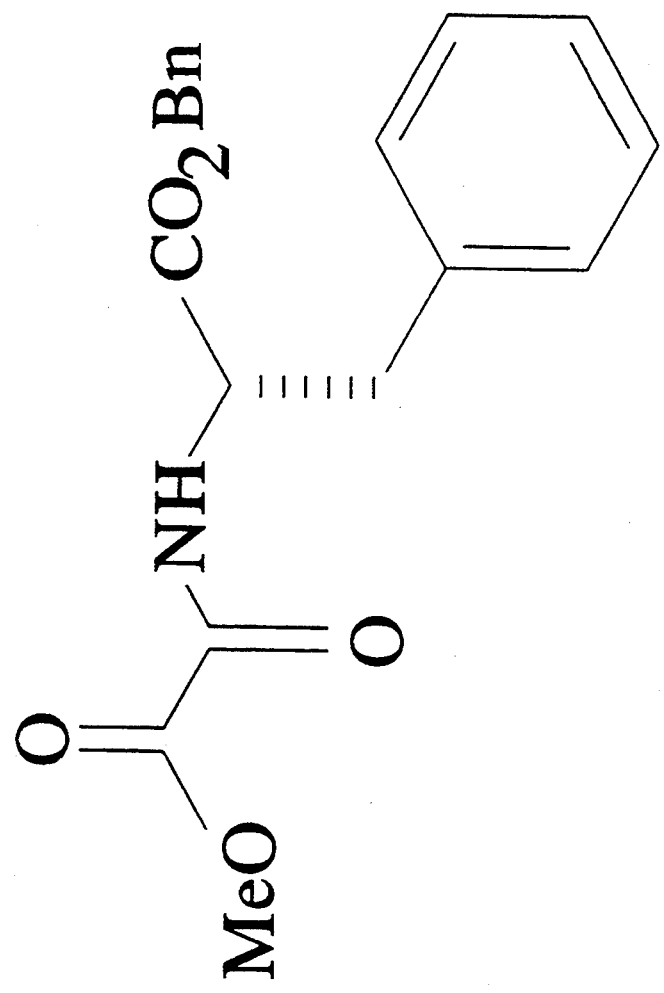
Figure 1G:
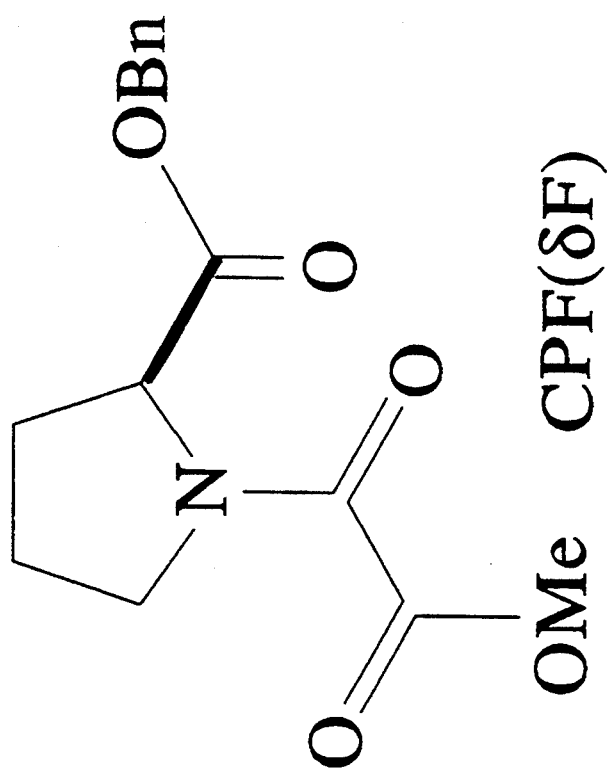

This invention relates to antiviral peptide compounds and to methods of inhibiting infection of human cells with viruses. This invention specifically relates to peptides that are chemically blocked at the amino- and carboxy termini with chemical protecting groups. In particular the invention relates to peptides comprising prolylalanine or prolylphenylalanine compounds that have antiviral activity. The invention is specifically directed to methods for preventing infection of human cells in vivo and in vitro with the human immunodeficiency virus HIV-1 and methods for treating in a human or humans infected with this and other viruses.

It is an object of the present invention to provide peptides of the following general structure:

$$A\text{-}X_n\text{-}Pro\text{-}Y\text{-}(Leu)_d\text{-}Z_m\text{-}E \text{ (SEQ. ID. No.:11)}$$

wherein X and Z can be any amino acid;
$m = 0, 1, 2, 3 \ldots$;
$n = 0, 1, 2, 3 \ldots$;
$d = 0$ or $1$;
A = N-carbomethoxycarbonyl or N-butoxycarbonyl;
B = methyl ester (OMe) or benzyl ester (OBn);
Y = alanine, phenylalanine or substituted phenylalanine;
wherein the amino acids are each individually in either the D or L stereochemical configuration and wherein the peptide has antiviral properties.

It is an object of the present invention to provide peptides of this general formula that have antiviral activity. It is a particular object of the present invention to provide peptides with antiviral activity against the human immunodeficiency viruses (HIV-1 and HIV-2).

It is an object of the present invention to provide peptides that prevent infection of cells with viruses. It is a particular object of the present invention that the cells protected from viral infection by the peptides are human cells. It is another object of the present invention that the virus infection is an HIV-1 infection.

It is an object of the present invention to provide peptides wherein the amino (N-) terminus of the peptide is protected from chemical or enzymatic degradation by virtue of having a chemical protecting group covalently linked thereto. It is a particular object of the present invention to provide peptides wherein the chemical protecting group is N-carbomethoxylcarbonyl.

It is an object of the present invention to provide peptides wherein the carboxyl (C-) terminus of the peptide is protected from chemical or enzymatic degradation by virtue of having a chemical protecting group covalently linked thereto. It is a particular object of the present invention to provide peptides wherein the chemical protecting group is benzyl ester. It is an additional object of the present invention to provide peptides wherein the chemical protecting group is methyl ester.

It is an object of the present invention to provide a peptide having antiviral properties that is N-carbomethoxycarbonyl-(D)-prolyl-(D)-phenylalanyl-benzyl ester.

It is an object of the present invention to provide a peptide having antiviral properties that is N-carbomethoxycarbonyl-(D)-prolyl-(L)-phenylalanyl-benzyl ester.

It is an object of the present invention to provide a peptide having antiviral properties that is N-carbomethoxycarbonyl-(L)-prolyl-(D)-phenylalanyl-benzyl ester.

It is an object of the present invention to provide a peptide having antiviral properties that is N-carbomethoxycarbonyl-(L)-prolyl-(L)-phenylalanyl-benzyl ester.

It is an object of the present invention to provide a peptide having antiviral properties that is N-carbomethoxycarbonyl-(L)-prolyl-(L)-phenylalanyl-methyl ester.

It is an object of the present invention to provide a peptide having antiviral properties that is N-carbomethoxycarbonyl-(D)-prolyl-(L)-alanyl-benzyl ester.

It is an object of the present invention to provide a peptide having antiviral properties that is N-carbomethoxycarbonyl-(D)-prolyl-(L)-alanyl-methyl ester.

It is an object of the present invention to provide a peptide having antiviral properties that is N-carbomethoxycarbonyl-(D)-prolyl-(D)-phenylalanyl-(L)-leucyl-benzyl ester.

It is an object of the present invention to provide a peptide having antiviral properties that is N-carbomethoxycarbonyl-(D)-prolyl-(L)-alanyl-(L)-leucyl-benzyl ester.

It is an object of the present invention to provide cyclic peptides of the following general structure:

$$\boxed{X_n\text{—Pro—Y—}(Leu)_d\text{—}Z_m} \text{ (SEQ ID No.: 12)}$$

wherein X and Z can be any amino acid;
$m = 4, 5, 6, 7 \ldots$;
$n = 4, 5, 6, 7 \ldots$;
$d = 0$ or $1$;
Y = alanine, phenylalanine or substituted phenylalanine;

wherein the amino acids are each individually in either the D or L stereochemical configuration and wherein the peptide has antiviral properties.

It is a object of the present invention to provide cyclic peptides of this general formula that have antiviral activity. It is a particular object of the present invention to provide peptides with antiviral activity against HIV-1 and HIV-2.

It is an object of the present invention to provide peptides that specifically bind to viral proteins. In a preferred embodiment, the virus is HIV-1. In another preferred embodiment, the viral protein is gp120.

It is an object of the present invention to provide peptides that prevent infection of cells with viruses. It is a particular object of the present invention that the cells protected from viral infection by the peptides provided by the invention are human cells. In an additional preferred embodiment, the human cells are hematopoietic cells. In a preferred embodiment, the human hamatopoietic cells are T lymphocytes (T cells). In the most preferred embodiment, the human T cells are T cells that express the cell surface antigen CD4.

It is an additional object of the present invention to provide a pharmaceutically acceptable composition having antiviral properties comprised of an therapeutically effective amount of the peptides provided by the present invention and a pharmaceutically acceptable carrier or diluent.

It is an object of the present invention to provide a method for inhibiting viral infection of human cells comprised of contacting the virus with the peptides provided by the invention. In a preferred embodiment, the virus is HIV-1. In an additional preferred embodiment, the human cells are hematopoietic cells. In a preferred embodiment, the human hematopoietic cells are T lymphocytes (T cells). In the most preferred embodiment, the human T cells are T cells that express the cell surface antigen CD4.

It is an object of the present invention to provide a method for inhibiting viral infection in a human comprised of administering a therapeutically effective dose of the peptides provided by the invention in a pharmaceutically acceptable carrier. In a preferred embodiment, the viral infection is an HIV-1 infection.

It is an additional object of the present invention to provide a pharmaceutically acceptable composition effective in inhibiting viral infection of human cells comprised of an effective amount of the peptides provided by the present invention and a pharmaceutically acceptable carrier or diluent.

It is an object of the present invention to provide a method of treating a human infected with a virus comprised of administering a therapeutically effective dose of the peptides provided by the invention in a pharmaceutically acceptable carrier. In a preferred embodiment, the viral infection is an HIV-1 infection.

It is an additional object of the present invention to provide a pharmaceutically acceptable composition effective in treating a human with a viral infection comprised of an effective amount of the peptides provided by the present invention and a pharmaceutically acceptable carrier or diluent.

It is an object of the present invention to provide a method of treating a human infected with a virus comprised of administering a therapeutically effective dose of the peptides provided by the invention and an effective amount of a second antiviral compound in a pharmaceutically acceptable carrier. In a preferred embodiment, the viral infection is an HIV-1 infection. In another preferred embodiment, the second antiviral compound is azidothymidine.

It is an additional object of the present invention to provide a pharmaceutically acceptable composition effective in treating a human with a viral infection comprised of an effective amount of the peptides provided by the present invention and an effective amount of a second antiviral compound in a pharmaceutically acceptable carrier or diluent. In a preferred embodiment, the second antiviral compound is azidothymidine.

It is an object of the present invention to provide a method of essentially destroying a virus comprised of contacting the virus with an effective amount of the peptides provided by the invention. In a preferred embodiment, the virus is HIV-1.

It is an object of the present invention to provide a method of essentially inactivating a virus in a human with a viral infection comprised of administering a therapeutically effective dose of the peptides provided by the invention in a pharmaceutically acceptable carrier. In a preferred embodiment, the virus is HIV-1.

It is an additional object of the present invention to provide a pharmaceutically acceptable composition effective for inactivating a virus in a human with a viral infection comprised of an effective amount of the peptides provided by the present invention and a pharmaceutically acceptable carrier or diluent.

It is an object of the present invention to provide a method for treating immunosuppression in a human associated with a viral infection comprised of administering a therapeutically effective dose of the peptides provided by the invention in a pharmaceutically acceptable carrier. In a preferred embodiment, the viral infection is an HIV-1 infection.

It is an additional object of the present invention to provide a pharmaceutically acceptable composition effective in treating virus-associated immunosuppression in a human comprised of an effective amount of the peptides provided by the present invention and a pharmaceutically acceptable carrier or diluent.

It is an object of the present invention to provide a method for diagnosing a viral infection in an animal, the method comprising the following steps:

(a) providing a first mixture comprised of the peptide of claim 1 or 2, a second mixture comprised of a standard amount of a viral protein that binds to the peptide according to claim 1 or 2, and a third mixture comprised of a diagnostically-significant tissue sample or bodily fluid;

(b) providing a specific binding reaction mixture by contacting the first, second and third provided mixtures;

(c) incubating the reaction mixture for a time sufficient to allow binding between the peptide according to claim 1 or 2 with the viral protein present in the second provided mixture and the third provided mixture;

(d) detecting the extent of the binding reaction by determining the amount of the standard viral protein bound to the peptide according to claim 1 or 2; and (e) determining the extent of viral infection by comparing the amount of binding of the standard viral protein to the peptide according to claim 1 or 2 in the presence of the tissue sample or bodily fluid of the third provided mixture with the amount of binding of the standard viral protein to the peptide according to claim 1 or 2 in the absence of the tissue sample or bodily fluid of the third provided mixture.

In a preferred embodiment of this method, the animal is a human. In an additional preferred embodiment, the virus is HIV-1. In another preferred embodiment, the viral protein is gp120.

It is an additional object of the present invention to provide a diagnostic reagent for detecting a vital infection in an animal wherein the reagent is comprised of the peptides provided by the invention.

Further objects and preferred embodiments of the present invention will be discussed in the following description of the preferred embodiments and claims.

DETAILED DESCRIPTION OF THE PREFERRED EMBODIMENTS

The present invention encompasses antiviral peptide compounds and methods for using such compounds. Specifically, the invention encompasses antiviral peptides chemically protected at the amino (N) and carboxyl (C) termini by the covalent attachment of chemical protecting groups. The invention specifically encompasses peptides comprised of prolylalanine or prolylphenylalanine compounds that have antiviral activity. The invention also encompasses methods for using these compounds for preventing HIV-1 infection of human cells in vivo and in vicro, and methods for treating humans infected with HIV-1 and other viruses.

The peptides provided by the present invention can be chemically synthesized by any of a number of manual or automated methods of synthesis known in the art. The preferred method of synthesis is from the component amino acids as described herein in Example 1. Automated synthetic routines such as those available for use with automated peptide synthesizers are also intended to come within the scope of the present invention. Chemical derivatization, using the methods disclosed in this specification or other methods well known in the art, of naturally-occurring peptides or peptides purified from mixtures of protein degradation products, degraded by enzymatic or chemical means, are also within the scope of this invention, as are peptides made by molecular or genetic engineering means.

The present invention provides peptides having antiviral properties wherein the N-terminus is protected from chemical or enzymatic degradation by virtue of having a chemical protecting group covalently linked thereto. Preferred chemical protecting groups used with the peptides of the present invention include but are not limited to N-tert-butoxycarbonyl and N-carbomethoxylcarbonyl. The most preferred N-terminal protecting group is N-carbomethoxylcarbonyl.

The present invention provides peptides having antiviral properties wherein the C-terminus is protected from chemical or enzymatic degradation by virtue of having a chemical protecting group covalently linked thereto. Preferred chemical protecting groups used with the peptides of the present invention include but are not limited to benzyl ester and methyl ester. The most preferred C-terminal protecting group is benzyl ester.

The present invention also provides cyclic peptides that have antiviral activity. These peptides provided by the invention are protected at the N- and C-terminal ends by the formation of peptide bonds.

The antiviral peptide compounds of the present invention include but are not limited to N-carbomethoxylcarbonyl-D-Pro-D-Phe-OBn [CPF(DD)], N-carbomethoxylcarbonyl-L-Pro-D-Phe-OBn [CPF(LD)], N-carbomethoxylcarbonyl-D-Pro-L-Phe-OBn [CPF(DL)], N-carbomethoxyl-carbonyl-L-Pro-L-Phe-OBn [CPF(LL)], N-carbomethoxylcarbonyl-D-Pro-L-Ala-OBn [CPF(F→A)], N-carbomethoxylcarbonyl-D-Pro-D-Phe-L-Leu-OBn [CPF(+Leu)], N-carbomethoxylcarbonyl-D-Pro-OBn [CPF($\delta$F)] and N-carbomethoxylcarbonyl-D-Phe-OBn [CPF($\delta$P)]. Preferred compounds include CPF(DD), CPF(DL), CPF(LD), and CPF(LL). The most preferred compound is CPF(DD).

The viruses envisioned to be targets of the antiviral activity include but are not limited to picornaviruses (e.g., poliovirus and rhinovirus); orthomyxoviruses (e.g., influenza virus); paramyxoviruses (e.g., measles virus and mumps virus); coronaviruses; rhabdoviruses (e.g., rabies virus and vesicular stomatitis virus); togaviruses (e.g., Semltki Forest virus and yellow fever virus); bunyaviruses (e.g., California encephalitis virus); arenaviruses (e.g., Lassa fever virus); rubella virus; reoviruses (e.g., Colorado tick fever virus); hepatitis viruses; adenoviruses; herpesviruses (e.g., herpes simplex virus); poxviruses (e.g., variola and vaccinia virus) and oncogenic viruses, including papilloma viruses, RNA tumor viruses, or retroviruses, and lentiviruses (e.g., human immune deficiency virus). The most preferred viruses are the human immunodeficiency viruses (HIV-1 and HIV-2).

Cells intended to be protected by the peptides provided by this invention include but are not limited to human, canine, bovine, murine, leporine, porcine, ovine, simian, feline, hircine, and equine. The preferred cells are human cells. More preferred cells are human T lymphocytes (T cells), and the most preferred human T cells are those human T cells expressing the cell surface antigen CD4.

The present invention also provides peptides that bind to viral protein. In a preferred embodiment, the viral protein is gp120 derived from HIV-1. In a preferred embodiment, binding is detected using a competitive binding assay as described in Example 2 herein.

The present invention provides a method of inhibiting infection of cells with virus. The preferred cells are human cells. More preferred cells are human T cells, and the most preferred cells are human T cells that express CD4. The preferred virus is HIV-1. The method provides contacting the virus with an amount of the peptides provided by the invention effective in inhibiting viral infection. Preferred concentrations of peptides are 50–800 $\mu$M, more preferred concentrations are 80–800 $\mu$M, the most preferred concentrations are 100–800 $\mu$M. Preferred peptides are CPF(DD), CPD(DL), CPF(LD), and CPF(LL). The most preferred compound is CPF(DD).

The present invention provides a method of preventing viral infection from spreading from infected cells to uninfected cells. Preferred cells are human cells. More preferred cells are human T cells, and the most preferred cells are human T cells that express CD4. The preferred virus is HIV-1. The method provides contacting the virus with an amount of the peptides provided by the invention effective in inhibiting the spread of the viral infection. Preferred concentrations of peptides are 50–800 $\mu$M, more preferred concentrations are 70–800 $\mu$M, the most preferred concentrations are 80–800 $\mu$M. Preferred peptides are CPF(DD), CPD(DL), CPF(LD), and CPF(LL). The most preferred compound is CPF(DD).

The present invention provides a method of essentially inactivating a virus comprised of contacting the virus with an effective amount of the peptides provided by the invention. The preferred virus is HIV-1. Preferred concentrations of peptides are 50–800 μM, more preferred concentrations are 300–500 μM and the most preferred concentration is 400 μM.

The methods of the present invention may be used to treat donated human blood or plasma to protect transfusion recipients from viral infection from contaminating virus. The methods of the present invention may be used to treat human semen to protect embryos derived from such semen, and mothers bearing such embryos or impregnated with such semen, from contaminating virus. In a preferred embodiment, the contaminating virus is HIV-1.

The invention also provides a method for diagnosing a viral infection in an animal. In one embodiment of this method, the viral infection is detected by competitive binding to peptides provided by the invention between an standard amount of a viral protein and an unknown amount of this viral protein present in a diagnostically significant tissue sample or bodily fluid. Methods for detecting competitive binding between a known amount of a protein and an unknown amount present in a diagnostically significant tissue sample or bodily fluid are well known in the art. Such methods include but are not limited to radioimmunoassay, competitive radioactive tracer molecule assay, and fluorescence-based techniques. Other methods of using this embodiment of the invention are intended to fall within the scope of the claims.

The present invention provides methods for inhibiting viral infection in a human. The invention also provides for treating a human infected with a virus. An additional embodiment of the present invention provides a method for essentially destroying virus present in a human. Another embodiment of the present invention includes methods for treating immunosuppression in a human associated with viral infection. Yet another embodiment of the present invention provides a method of prophylaxis for treating a human exposed to infection with a virus, in particular those directly at risk of infection as a result of intimate contact with humans infected with a virus of tissues or bodily fluids contaminated by a virus. The preferred virus of these embodiments of the invention is HIV-1. The invention provides pharmaceutically acceptable compositions effective for use with the methods provided By the invention comprising the peptides of the invention and a pharmaceutically acceptable carrier.

Preparation of pharmaceutically acceptable compositions of the peptides of the present invention can be accomplished using methods well known to those with skill in the art. Any of the common carriers such as sterile saline solution, plasma, etc., can be utilized with the peptides provided by the invention. Routes of administration include but are not limited to oral, intravenous, parenteral, rectal, optical, aural and transdermal. Peptides of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The following examples describe certain specific embodiments of the invention. However, many additional embodiments not described herein nevertheless fall within the spirit and scope of the present invention and claims.

EXAMPLE 1

In vitro Synthesis of Peptides Having Antiviral Properties

The compounds of the invention were made by conventional chemical procedures (M. Bodanszky, *Principles of Peptide Synthesis,* Springer-Verlag:New York, 1984) utilizing the appropriate amino acids, including proline (Pro or P), alanine (Ala or A), phenylalanine (Phe or F) or substituted phenylalanine (Phe-Z) and leucine (Leu or L) in the D- or L- stereochemical conformation and using conventional blocking agents (Bodansky, ibid.)

The N-blocked tertiary butoxycarbonyl (Boc)-derivatives of Pro, Leu, Ala and Phe were prepared from the D- or L- stereochemical isomers of these amino acids, and then estertfied with either benzyl alcohol (OBn) or methyl alcohol (OMe) to block the carboxyl terminus. The preparation of N-Boc-Phe-OBn is described to illustrate the methods used.

To a solution of D-phenylalanine (1.21 g, 7.32 mmol) and triethylamine (1.53 ml, 11.0 mmol) in 1:1 acetone:water (73.2 ml) was added Boc-ON (1.98 g, 8.06 mmol) and the reaction mixture was stirred at room temperature for 4 hours. Acetone was removed by evaporation under reduced pressure, and the resulting aqueous solution was diluted with a solution of saturated sodium bicarbonate and washed with ether. The remaining aqueous layer was acidified to a pH of 2.0 and extensively extracted with ethyl acetate. The combined organic layers were dried over magnesium sulfate ($MgSO_4$) and concentrated to yield 1.99 E of a clear glassy solid that is N-Boc-D-Phe.

Dimethylaminopropylethylcarbodiimide (EDC) (1.68 E, 8.78mmol) was added to a solution of the crude N-Boc-D-Phe (as described previously, assumed to be 7.32 mmol), benzyl alcohol (1.14 ml, 11.0 mmol) and 4-pyrrollidinopyridine (217 mg, 1.46 mmol) in dichloromethane (73.2 ml). The reaction mixture was stirred at room temperature overnight, diluted with dichloromethane, and washed sequentially with a dilute solution of HCl (<5%, pH 3.0), a solution of saturated sodium bicarbonate, and brine. The combined organic layers were dried over $MgSO_4$ and concentrated to obtain a yellow oil. This substance was subjected to silica gel chromatography, eluted with a solution that was 5:1 hexanes:ethyl acetate, and resulted in a yield of 2.31 g of N-Boc-D-Phe-OBn.

Peptides were synthesized in vitro using protected amino acids prepared as described above. Synthesis was performed by standard techniques (Bodanszky, ibid.), which are herein illustrated by a description of the synthesis of N-Boc-D-Pro-D-Phe-OBn.

Distilled trifluoroacetic acid (TFA; 5.33 ml, 69.2 mmol) was added dropwise to a solution of N-Boc-D-Phe-OBn (614 mg, 1.73mmol), prepared as described above, in dry dichloromethane (6.0 ml), and the mixture was stirred at room temperature for 4 hours. TFA and solvent were then removed by evaporation under reduced pressure, resulting in the crude trifluoroacetate salt of D-Phe-OBn as a white crystalline solid, which was used without further purification.

EDC (1.68 g, 8.78 mmol) was added to a solution of N-Boc-D-Pro (372 mg, 1.73 mmol) and hydroxybenzotriazole (281 mg, 2.08 mmol) in dry dichloromethane (17.3 ml) and the resulting mixture was stirred at room temperature for 2.5 hours. Distilled triethylamine (482 μl, 3.46 mmol) was then added, followed by the crude trifluoroacetate salt of D-Phe-OBn, prepared as described above. The solution was stirred for an additional 3 hours, diluted with dichloromethane and washed sequentially with a dilute solution of HCl (<5%, pH 3.0), a solution of saturated sodium bicarbonate, and brine. The combined organic layers were dried over $MgSO_4$ and concentrated to obtain a yellow oil. This substance was subjected to silica gel chromatography, eluted with a solution that was 2:1 hexanes:ethyl acetate, and resulted in a yield of 658 mg of N-Boc-D-Pro-D-Phe-OBn as a clear oil.

The final step in the preparation of the peptides of the present invention is the substitution of N-carbomethoxycarbonyl for the N-Boc protecting group at the amino terminus of the peptide. The method used for this substitution will be illustrated by a description of the preparation of N-carbomethoxycarbonyl-D-Pro-D-Phe-OBn [CPF(DD)] from N-Boc-D-Pro-D-Phe-OBn, prepared as described above.

Distilled TFA (4.60 ml, 59.6 mmol) was added dropwise to a solution of N-Boc-D-Pro-D-Phe-OBn (2.70 g, 5.96 mmol) in dry dichloromethane (5.0 ml), and the mixture was stirred at room temperature for 4 hours. TFA and solvent were then removed by evaporation under reduced pressure, and the resulting residue redissolved in chloroform. Water and solid potassium carbonate were added in amounts sufficient to achieve & pH of 10 in the resulting aqueous solution, and the aqueous layer was then extensively extracted with chloroform. The combined organic layers were dried over $MgSO_4$ and concentrated to yield crude D-Pro-D-Phe-OBn as a yellow oil which was used without further purification.

A solution of crude D-Pro-D-Phe-OBn (assumed to be 5.96 mmol), distilled triethylamine (4.15 ml, 29.8 mmol) and dimethylaminopyridine (one crystal) in dichloromethane (60 ml) was cooled to 0° C. in an ice-water bath. Methyl oxalyl chloride (0.822 ml, 8.9 mmol) was added dropwise, and the reaction mixture stirred for 2 hours (during which time the ice-water bath was allowed to warm to room temperature). The reaction was quenched by the addition of saturated sodium bicarbonate solution, diluted with chloroform, and washed sequentially with a dilute solution of HCl (<5%, pH 3.0), a solution of saturated sodium bicarbonate, and brine. The combined organic layers were dried over $MgSO_4$ and concentrated to obtain a yellow oil. This substance was subjected to silica gel chromatography, eluted with a solution that was 1:1 hexanes:ethyl acetate, and resulted in a white solid that was recrystallized (2:1 hexanes:ethyl acetate) to yield 1.58 g of N-carbomethoxylcarbonyl-D-Pro-D-Phe-OBn [CPF(DD)] as a white solid.

The compounds made using the methods described above include but are not limited to N-carbomethoxylcarbonyl-D-Pro-D-Phe-OBn [CPF(DD)], N-carbomethoxylcarbonyl-L-Pro-D-Phe-OBn [CPF(LD)], N-carbomethoxylcarbonyl-D-Pro-L-Phe-OBn [CPF(DL)], N-carbomethoxyl-carbonyl-L-Pro-L-Phe-OBn [CPF(LL)], N-carbomethoxylcarbonyl-D-Pro-D-Ala-OBn [CPF(F→A)], N-carbomethoxylcarbonyl-D-Pro-D-Phe-L-Leu-OBn [CPF(+Leu)], N-carbomethoxylcarbonyl-D-Pro-OBn [CPF(δF)] and N-carbomethoxylcarbonyl-D-Phe-OBn [CPF(δP)]

In the alternative, peptides were synthesized having methyl ester as a C-terminus protecting group. The synthesis of these peptides is illustrated by the following description of the synthesis of N-carbomethoxycarbonyl-L-Pro-L-Phe-OMe [CPF(C-Me)].

To a solution of L-Pro-L-Phe (1.0 g, 3.8 mmol) and triethylamine (0,794 ml, 5.7 mmol) in 1:1 water:acetone (38 ml) was added Boc-ON (1.13 g, 4.6 mmol), and the reaction mixture stirred at room temperature for 9 hours. Acetone was removed by evaporation under reduced pressure and the resulting aqueous solution diluted with a solution of saturated sodium bicarbonate and then washed with ether. The remaining aqueous phase was acidified to pH 2.0 and extensively extracted with ethyl acetate. The combined organic layers were dried over $MgSO_4$ and concentrated to yield 1.99 g of N-Boc-L-Pro-L-Phe as a white glassy solid.

Diazomethane was generated by the addition of Diazald (234 mg, 1.1 mmol) to a solution of potassium hydroxide (1 g, 17.8 mmol) in 95:5 ethanol:water (50 ml) and transferred by a stream of argon gas to a solution of N-Boc-L-Pro-L-Phe (20 mg, 0.54 mmol), prepared as described above, in dichloromethane (7.0 ml). Solvent was then removed under vacuum followed by silica gel column chromatography, eluted with 3:2 hexanes:ethyl acetate, yielding 196.1 mg of the desired product, N-Boc-L-Pro-L-Phe-OMe as a white solid.

The N-Boc-L-Pro-L-Phe-OMe prepared as described was converted to the N-carbomethoxycarbonyl derivative as follows. Distilled TFA (1.48 ml, 19.3 mmol) was added dropwise to a solution of N-Boc-L-Pro-L-Phe-OMe (184 mg, 0.48 mmol) in dry dichloromethane (1.5 ml) and the mixture stirred at room temperature for 3 hours. Solvent and excess TFA were removed by evaporation under reduced pressure, and the resulting crude TFA salt of L-Pro-L-Phe-OMe was used without further purification.

A solution of crude L-Pro-L-Phe-OMe, distilled triethylamine (1.34 ml, 9.64 mmol) and diethylaminopyridine (one crystal) in dichloromethane (5.0 ml) was cooled to 0° C. in an ice-water bath. Methyl oxalyl chloride (0.22 ml, 2.4 mmol) was added dropwise, and the reaction mixture stirred for 50 minutes (during which time the ice-water bath was allowed to warm to room temperature). The reaction was quenched by the addition of saturated sodium bicarbonate solution, diluted with chloroform, and washed sequentially with a dilute solution of HCl (<5%, pH 3.0), a solution of saturated sodium bicarbonate, and brine. The combined organic layers were dried over $MgSO_2$ and concentrated to obtain a brown oil. This substance was subjected to silica gel chromatography, eluted with a solution that was 1:2 hexanes:ethyl acetate, and resulted in a yield of 142 mg of N-carbomethoxylcarbonyl-L-Pro-L-Phe-OMe [CPF(C-Me)] as a clear oil.

Peptides made by the above methods were dissolved in dimethylsulfoxide (DMSO) at a concentration of 8 mg/ml and stored at 0° C. until use. The chemical structures described in this Example are illustrated in FIGS. 1A through 1G.

EXAMPLE 2

Characterization of Dipeptide Binding to Human Immunodeficiency Virus Glycoprotein gp120

The peptides prepared as described in Example 1 were characterized as to their ability to bind to the human immunodeficiency virus (HIV-1) glycoprotein gp120. This ability was assayed on the basis of the peptides ability to inhibit binding of gp120 to the human CD4 protein.

On the day of the assay the peptides were diluted 10-fold in phosphate buffered saline (PBS) and 2-fold serial dilutions made into PBS previously adjusted to the same DMSO concentration (10%). 25 μl each of each peptide solution and a solution of gp120 (20 μg/ml) (synthesized in vitro from baculovirus and obtained from MicroGeneSys, West Haven, Conn.) were combined and incubated at 37° C. for 1 hour. A total of $3-5 \times 10^5$ HSBCD4-M.23 cells [derived from a clone of the pre-T cell leukemia line HSB-2 (obtained from the American Type Culture Collection (ATCC), Rockville, Md.) which expresses human CD4 as a result of transfaction of CD4 cDNA sequences; Diamond et al., *Proc. Natl. Acad. Sci.* 87: xxxx (1990)] were pelleted in the walls of a 96-well V-bottom microtiter plate, resuspended with the preincubated gp 120-peptide mixture and allowed to incubate at 4° C. for 1 hour. The cells were then pelleted and resuspended in 50μl of a solution containing rabbit anti-gp120 antibody (diluted 1:400 in PBS; MicroGeneSys, West Haven, Conn.) and incubated at 4° C. for 30 min. The cells were again pelleted, washed with 100 μl PBS and resuspended in 50μl of a solution containing fluorescein isothiocyanate (FITC)-conjugated goat anti-rabbit antibody (diluted 1:20; Tago) and incubated at 4° C. for 30 min. The cells were pelleted and washed as before, and resuspended in 100 μl of a solution containing propidium iodine at a concentration of 25 μg/ml and transferred to tubes containing 400 μl PBS for flow cytometric analysis on an Epics V (Coulter) for FAtScan (Betton-Dickinson, Mountainview, Calif.). Cells were gated on propidium iodide to exclude dead cells. Green fluorescence was collected on the linear amplifier and the mean fluorescence calculated. Values were corrected by subtracting the mean fluorescence of cells treated with both antibodies but not exposed to gp 120, which did not differ significantly from the intrinsic fluorescence of the cells, and was generally <15 (arbitrary units). The baculovirus-produced gp120 was found to be sub-saturating at the concentration used (10 μl/ml) and the relation between fluorescence intensity and gp120 concentration in these experiments approached linearity.

The following peptides, prepared as described in Example 1 were tested:
1. N-carbomethoxycarbonylprolylphenylalanylbenzylester [CPF(LL)]
2. N-carbomechoxycarbonylprolylphenylalanylbenzylester [CPF(DD)]
3. N-carbomethoxycarbonylprolylphenylalanylbenzylester [CPF(LD)]
4. N-carbomethoxycarbonylprolylphenylalanylbenzylester [CPF(DL)]
5. N-carbomethoxycarbonylprolylphenylalanylleucylbenzyl ester [CPF(+Leu)]
6. N-carbomethoxycarbonylprolylalanylbenzylester [CPF(F→a)]
7. N-carbomethoxycarbonylprolylphenylalanylmethylester ([CPF(C-Me)]
8. N-carbomethoxycarbonylphenylalanylbenzylester [CPF(δP)]
9. N-carbomethoxycarbonylprolylbenzylester [CPF(δF)]
10. N-butoxycarbonylprolylphenylalanylbenzylester [CPF(N Boc)]

Figure 2A:
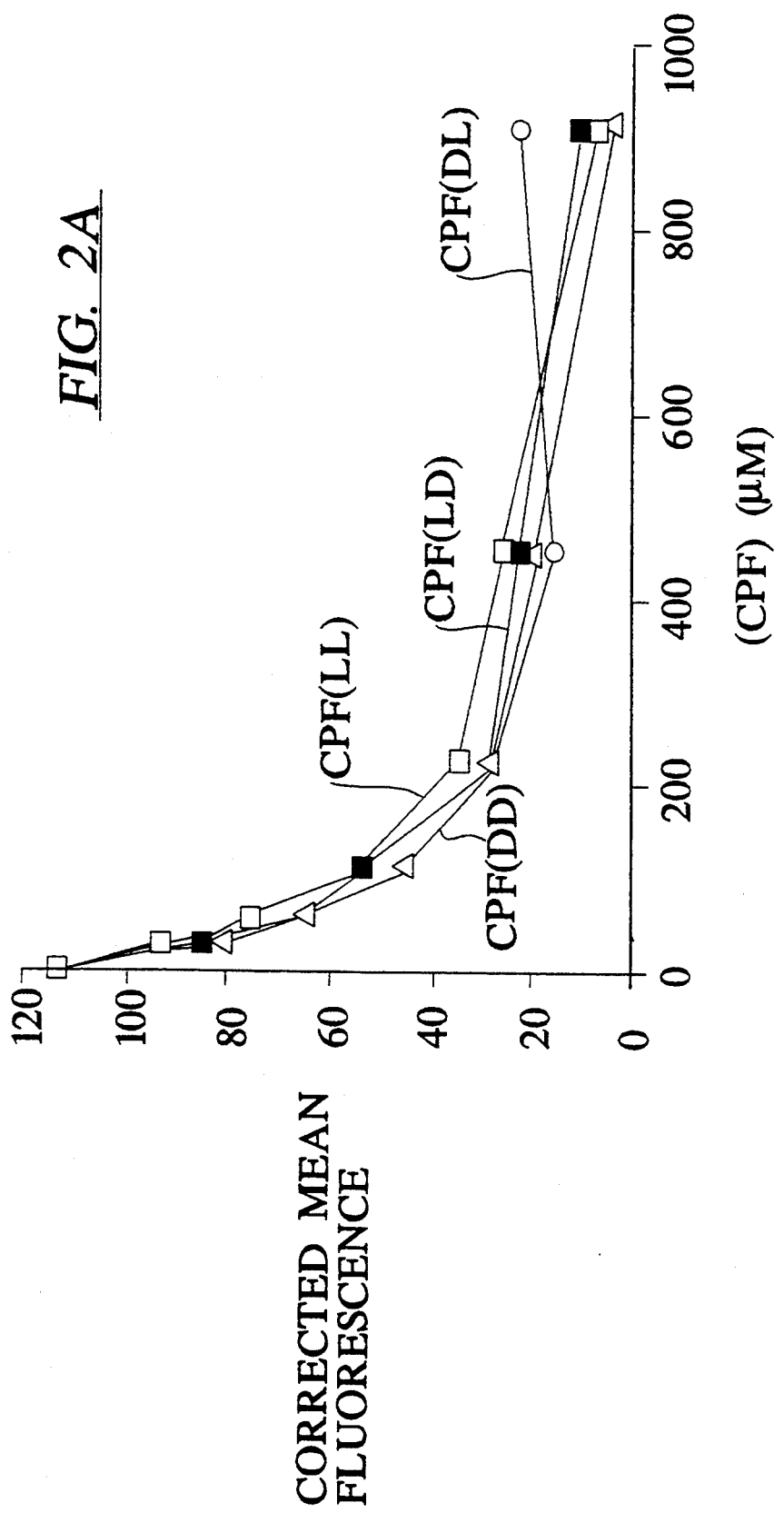
FIG. 2A-2C illustrates the inhibitory effect of incubation with the peptides of the invention on HIV-1 gp120 binding to CD4.
Figure 2B:
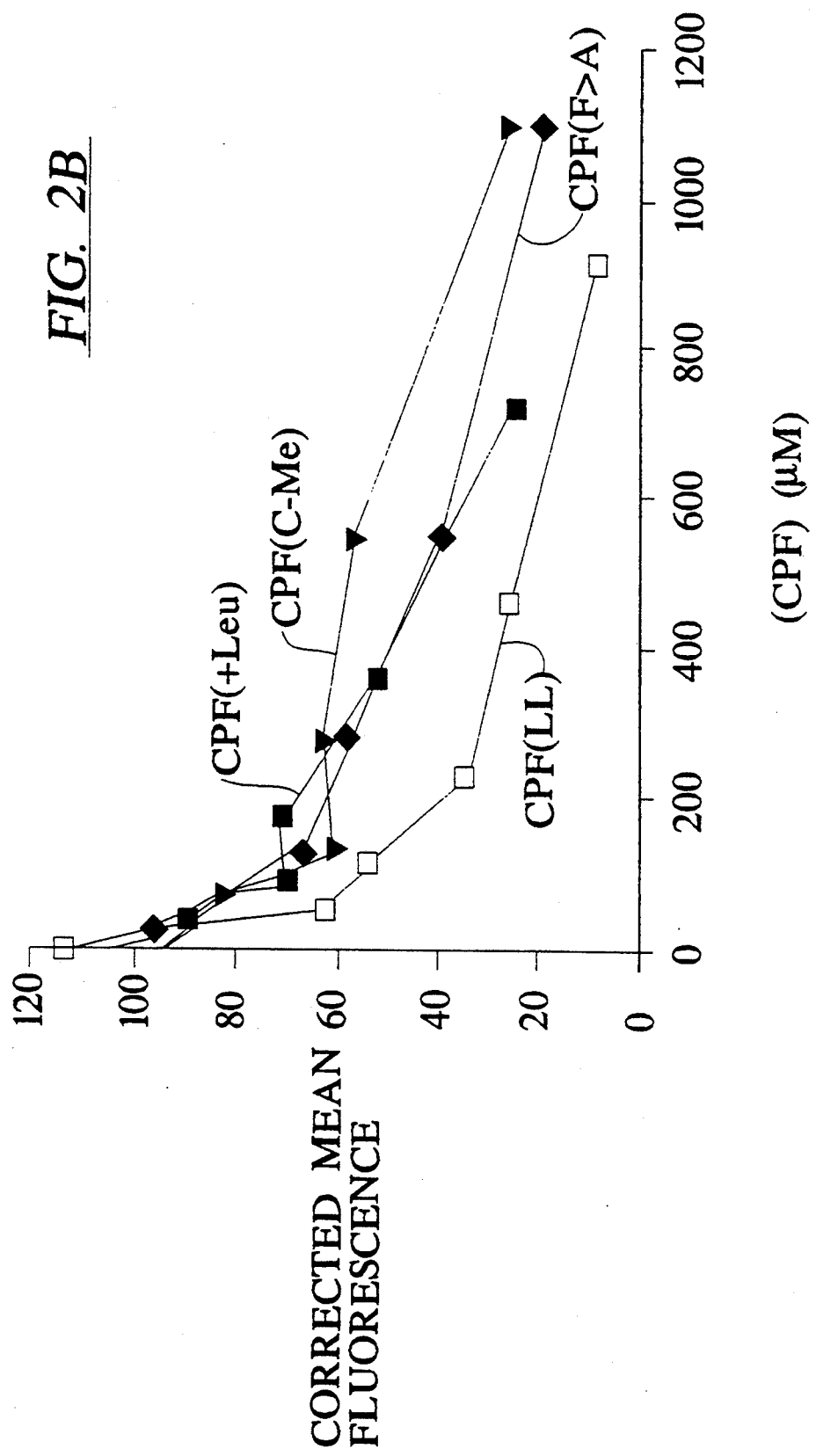
Figure 2C:
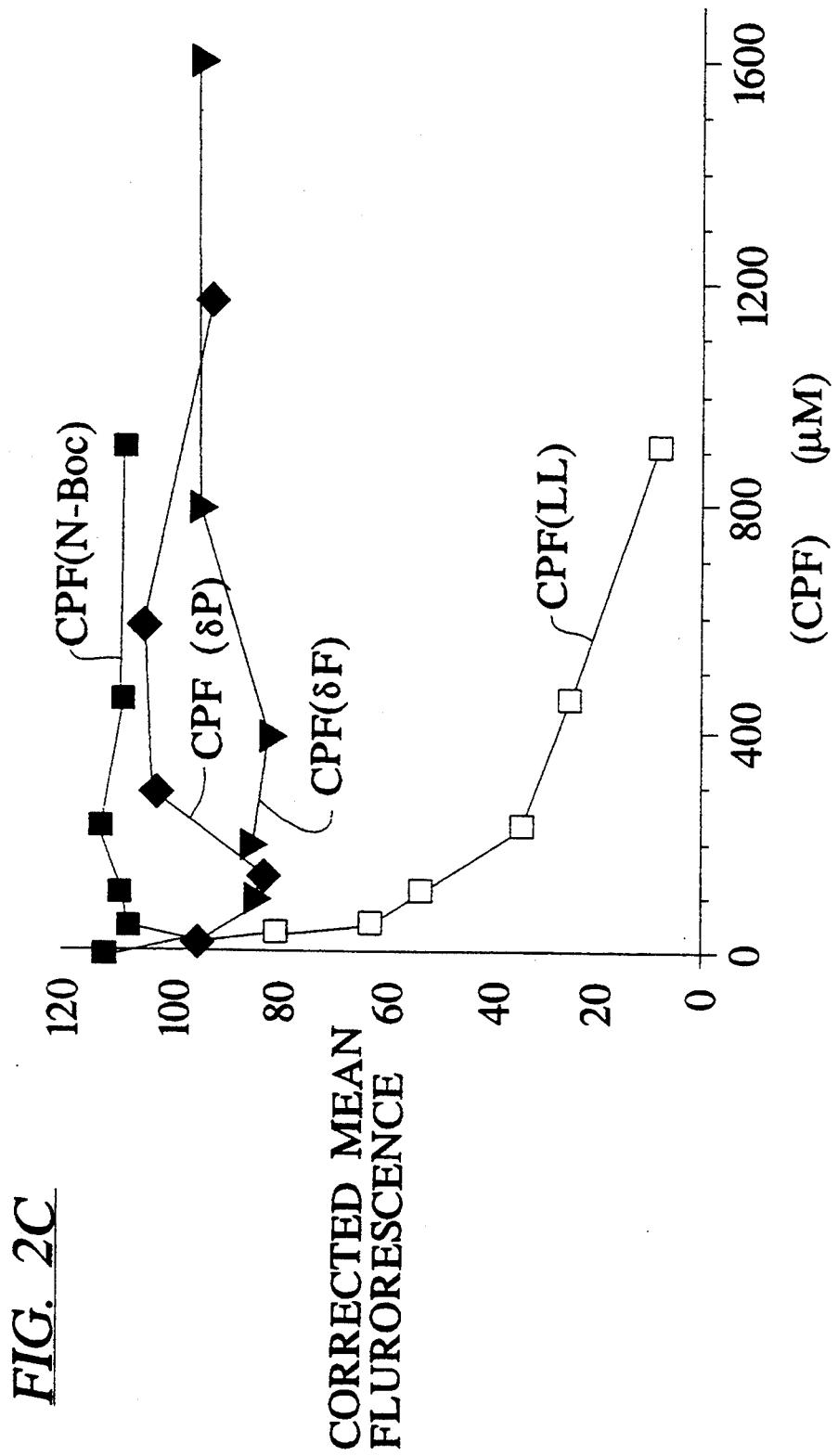

The results of these experiments are shown in FIG. 2A-2C. FIG. 2A shows the values of the corrected mean fluorescence of CD4-expressing cells incubated with gp120 that had been pre-treated with peptides CPF(DD), CPF(LL), CPF(DL), and CPF(LD). For each peptide tested, the corrected mean fluorescence value decreased as the concentration of the peptide increased from about 50 μM to 900 μM. This result indicates that each of these peptides is capable of inhibiting the binding of gp120 to purified CD4.

In FIG. 2B the results of the experiments using the peptides CPF(LL), CPF(F→A), CPF(CMe), and CPF(+Leu) are presented. In comparison with CPF(LL), the ability of the other peptides to inhibit gp120 binding to CD4 expressed on the surface of human HSBCD4-M.23 cells is shown to be 2-5-fold weaker, as indicated by the finding that the concentrations of these peptides which results in 50% inhibition of gp120 binding must be 2-5-fold higher than the concentrations of CPF(LL) required to achieve 50% inhibition levels.

FIG. 2C presents the results of these experiments using the peptides CPF(N-Boc), CPF(δP) and CPF(δF); CPF(LL) is included for comparison. The results of these experiments show that incubation of gp120 with these peptides does not inhibit gp120 binding to CD4-expressing human cells, in contrast to the CPF(LL) peptide. This result indicates that both the prolyl and phenylalanyl residues are essential for inhibition of gp120 binding. In addition, the inability of CPF(N-Boc) to inhibit gp120 binding indicates that the particular N-terminus blocking agent used has functional significance for more than its ability to prevent chemical degradation of the peptide. Similarly negative results have been obtained using the N-acetyl analogs of CPF, and the trifluoroacetate salt of (DD) prolylphenylalanylbenzylester. These compounds were also found to be unable to inhibit gp120 binding to HBSCD4-M.23 cells.

The proposal that the mechanism of peptide inhibition of CD4-gp120 binding is mediated by binding of the peptide to gp120, as opposed to binding to CD4, is supported by results that preincubation of HBSCD4-M.23 cells in the presence of CPF(LL) at a concentration of 100 μg/ml did not affect staining of these cells with monoclonal antibodies (mAb) OKT4, OKT4C, OKT4D or Leu3A [Jameson et al., Science 240: 1335-1339 (1988)]. These antibodies are specific for the CD4 molecule; the latter 2 mAbs also block the binding of CD4 to gp120.

In order to establish with greater certainty that the inhibitory effect of peptide incubation with gp120 was the result of specific binding between the peptides and this protein, the binding characteristics of CPF(DD) were further characterized as follows. A 100 μl solution of gp120 at a concentration of 20 μg/ml was incubated at 37° C. for 1 hour in the presence or absence of 100 μl of CPF(DD) at concentrations between 50-800 μg/ml. 100 μl of a solution of 10% DMSO in PBS were added to samples incubated without the peptide as a control. 50 μl of each sample was then diluted to 1 ml with PBS and concentrated by ultrafiltration using a Centricon-30 ultrafiltration device (Amicon, Beverly, Mass.) having a molecular weight cutoff of 30,000 kilodaltons (kD). Ultrafiltration was performed by centrifugation at 5700 rpm (1500 g) for 20 minutes at 4° C. in an SA-600 rotor (Dupont, N. Billerica, Mass.). Centricons were pretreated with a solution of 1% casein to reduce non-specific binding of gp120 to the device. All samples were kept at 4° C. prior to analysis. Equivalent amounts of gp120 were recovered from experimental (+CPF) and control (−CPF) retentates, as confirmed by protein microassay.

Inhibition of gp120 binding to CD4 after incubation with CPF(DD) was analyzed as described above for both dilute and concentrated samples. Binding of gp120 to CD4 is inhibited to a similar extent both before and after dilution and ultrafiltration, as compared to untreated gp120. Moreover, the extent of this inhibition is greater than was obtained by simple incubation of gp120 with the same concentration of the peptide, as described above. Similar results were also obtained when the dilution and ultrafiltration process was repeated three times (sequentially), resulting in a final CPF dilution of more than 8000-fold. These results show that CPF(DD) binds specifically to gp120, remains bound during dilution and ultrafiltration and the binding of the peptide is not rapidly reversible.

EXAMPLE 3

Inhibition of HIV-1 Infection of Human Cells

Peptides prepared as described in Example 1 were used to inhibit infection of a human CD4-expressing T cell line, H9 (available from the American Type Culture Collection, Accession No. CRL 8543) human immunodeficiency virus (HIV-1 strains HTLV-III$_B$ or MN, obtained from the AIDS Research and Reference Reagent Program). HIV-1 used in these experiments was derived from supernatants of lo virally-infected H9 cells filtered through a 0.54 μ filter (Amicon, Beverly, Mass.) as described [Finberg ecal., Science 249: 287–291 (1990)]. Filtered supernatants having a viral titre of $1 \times 10^6$ tissue culture infectious units (TCIU)/ml were incubated with or without the addition of CPF(DD) prepared as described in Example 1 at concentrations of between 40–800 μM for 1 hour at 37° C. CPF peptides were dissolved in DMSO at 8 mg/ml and then diluted with RPMI 1640 media containing 10% fetal calf serum (FCS). One milliliter specimens of the virus-containing supernatant [in the presence or absence of CPF(DD)]were then contacted with $1 \times 10^6$ previously uninfected H9 cells at a multiplicity of infection of 10. After infection, cells were washed three times and used to seed fresh cultures of $10^5$ cells/ml in RPMI 1640/10% FCS; the cultures were maintained for a period of up to 12 days at a density of $5 \times 10^5$ cells/ml. Supernatants obtained 48 hours after the final passage of these cultures were analyzed for the amount of HIV-1 p24 antigen present as a measure of the extent of infection at three day intervals. p24 was detected using a commercially-available enzyme-linked immunosorbent assay (ELISA) kit (Abbott Labs, North Chicago, Ill.).

Figure 3A:
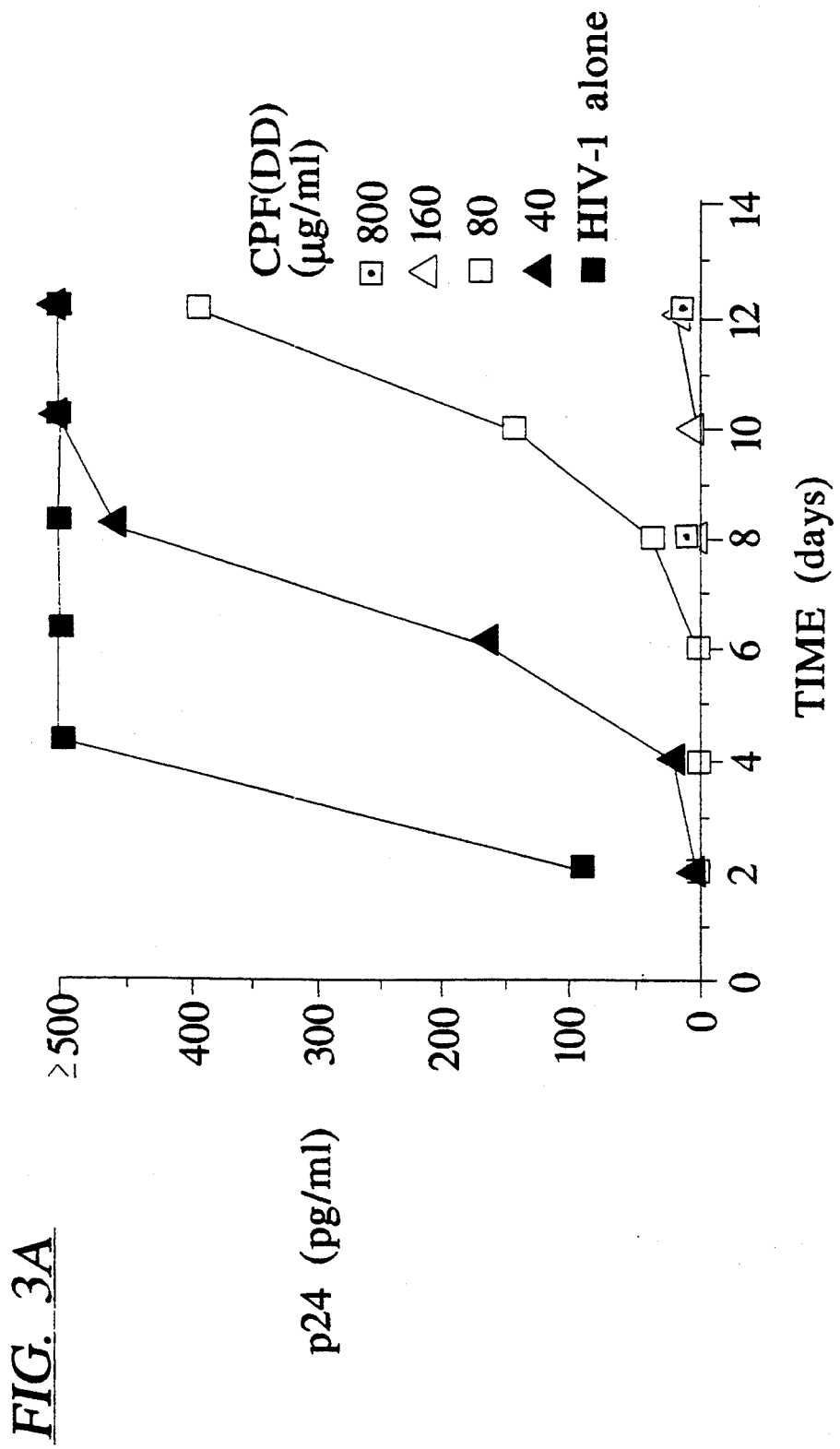
FIG. 3A-3C illustrates the inhibitory effect of incubation with the peptides of the invention on HIV-1 infection of human cells.
Figure 3B:
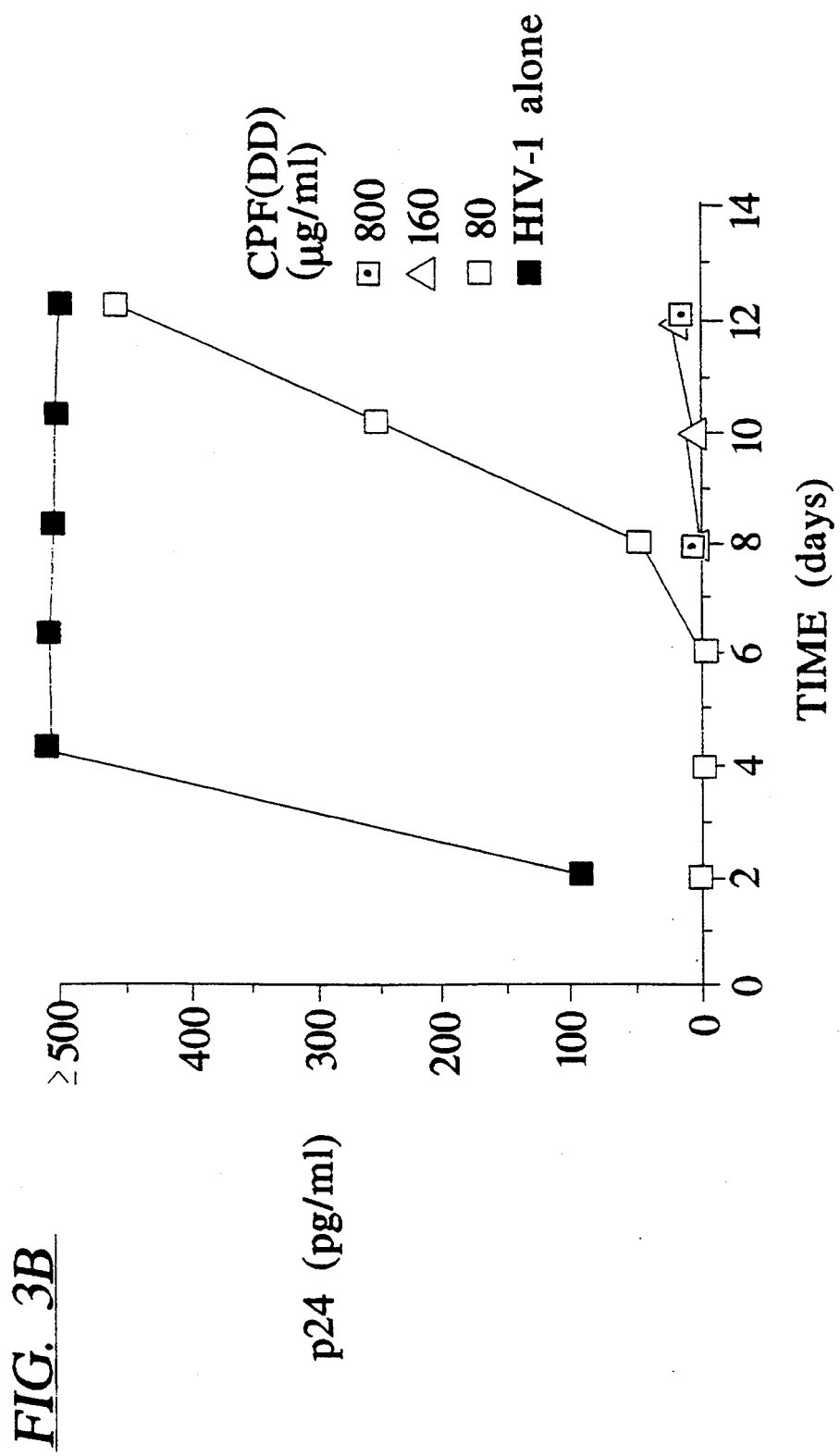
Figure 3C:
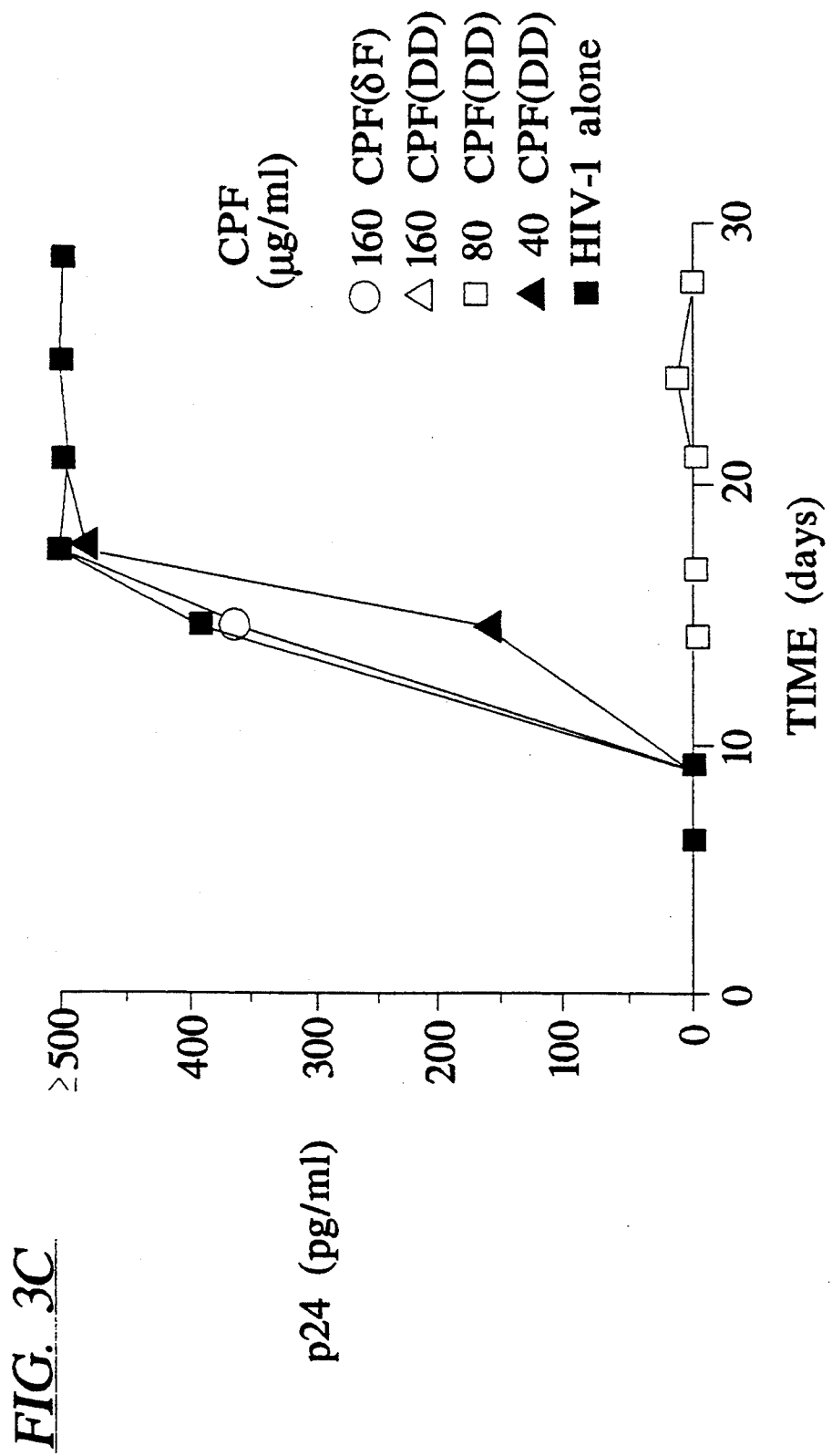

The results of these experiments are shown in FIG. 3A–3C. FIG. 3A shows the results obtained after incubation of increasing amount of the CPF(DD) peptide with HTLV-III$_B$ virus followed by infection of H9 cells. The extent of infection by HIV1 is represented by the amount of p24 antigen detected by ELISA. As is shown in the Figure, infection of H9 cells with virus without pre-incubation with CPF(DD) peptides results in the efficient production of p24 antigen which reaches a maximum at approximately three days after infection. Incubation of the virus with CPF(DD) at a concentration of 40 μg/ml delays the time of maximum p24 antigen production until 10 days post infection. Incubation of the virus with the peptide at 80 μg/ml inhibits the infection to the extent that the production of p24 antigen achieves less than 80% of the maximum over the 12 days of the experiment. At peptide concentrations greater than 100 μg/ml incubation of the virus with the peptide completely inhibits p24 antigen production in cells contacted with the virus. Similar results can be obtained with CPF(LL), CPF(LD) and CPF(DL) peptides.

The results presented in FIG. 3B represent the same experiment described above using the HTLV-MN strain of the virus. Similar results were obtained, indicating that the CPF(DD) peptide at concentrations of at least 100 μg/ml is able to completely inhibit viral antigen production, and presumably productive HIV infection, in a manner that is independent of the strain of virus used for the infection.

FIG. 3C presents the results of peptide inhibition experiments in which the cells used for infection were CD4-expressing human peripheral blood lymphocytes (PBL). These cells were obtained by depleting peripheral blood mononuclear cells isolated by passage through nylon wool [Finberg et al., Science 249: 287–291 (1990)]using antibodies specific for CD8 (OKTS, obtained from ATCC) and CD16 (B73.1, a gift of G. Trinchieri) followed by treatment with antibody-coated magnetic beads [Haregerwoin et al., Nature 340: 309 (1989)]. This treatment enriches the cell population for CD4-expressing human peripheral T cells. Virus was incubated for 1 hour at 37° C. with varying concentrations of CPF(DD), or with CPF(6F) at a concentration of 160 μg/ml. The treated virus preparation was then incubated with cells for 1 hour at 37° C. Cells were washed twice and maintained in RPMI 1640/10% FCS supplemented with interleukin 2 [10 units/ml, Collaborative Research]. Cells were maintained and assayed for p24 production as described above.

The results of these experiments are presented in FIG. 3C, indicate that human T cells derived from PBL are efficiently infected by HIV under these experimental conditions, and production of p24 antigen reaches a maximum after approximately 15 days. Incubation of HIV with CPF(DD) at a concentration of 40 μg/ml, or CPF(δF) at a concentration of 160 μg/ml, does not effect either the kinetics or the maximum production of p24 in these cells. In contrast, incubation of virus with CPF(DD) at concentrations of 80 g/ml and above completely inhibit HIV infection of human T cells as measured by the detection of p24 antigen. These results demonstrate that the effect of CFF peptides observed on cell lines in vitro can be reproduced using human T cells derived from PBL, and indicate that the inhibitory effect of CPF peptides on HIV infection may be useful in treating humans infected with HIV.

Figure 4:
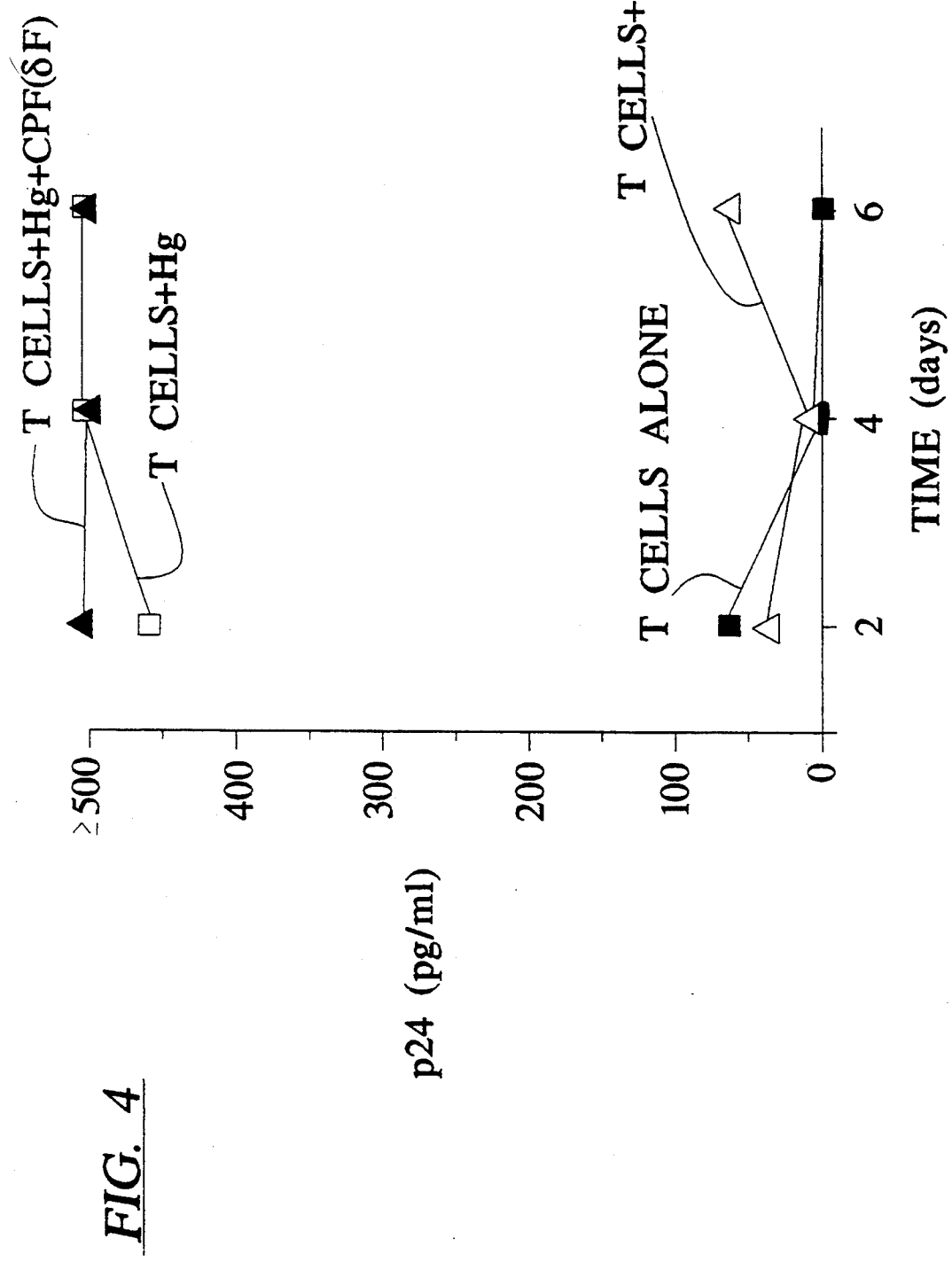
FIG. 4 illustrates the inhibitory effect of incubation with the peptides of the invention on the spread of HIV-1 from infected to uninfected cells in vitro.

Peptides prepared as described in Example 1 were also found to be able to inhibit the spread of HIV-1 from infected to non-infected human T cells. PBL-derived human T cells, infected with HIV-1, were washed extensively with RPMI 1640 media and then $10^4$ infected T cells were added to $5 \times 10^5$ uninfected H9 cells in the presence or absence of CPF(DD) or CPF(δF) at concentrations of 80 μg/ml. Cells were co-cultivated and maintained at H9 cell densities of $5\times10^5$ cells/ml and tested after 2, α and 6 days of co-cultivation. The extent of infection of H9 cells was determined by p24 antigen ELISA assay, performed 48 hours after washing the T-cell-H-9 cell mixture free of virus. The results of these experiments are shown in FIG. 4. The results presented in this Figure show the amount of p24 antigen present in the supernatant after co-cultivation for various times, as determined by ELISA assay. Co-cultivation of infected and uninfected cells in the presence of CPF(DD) results in the complete absence of p24 antigen after 4 days of co-cultivation. Co-cultivation of T cells and H9 cells in the presence of CPF(δF), on the other hand, results in p24 antigen levels no different from those detected in co-cultures of T cells and H9 cells incubated without peptides. These results indicate that CPF peptides are effective in preventing the spread of HIV from infected cells to uninfected cells, and suggests that this effect may be useful for treating HIV infections in vivo.

The effect of incubation of HIV-1 with CPF peptides on virus structure was examined by electron microscopy. HIV-1 prepared and isolated as described above was incubated at a titre of $10^6$ TCIU/ml with CPF(DD) at a concentration of 400 μg/ml at 37° C. for 1 hour. The virus preparations were then washed and prepared for electron microscopy by standard methods.

Figure 5A:
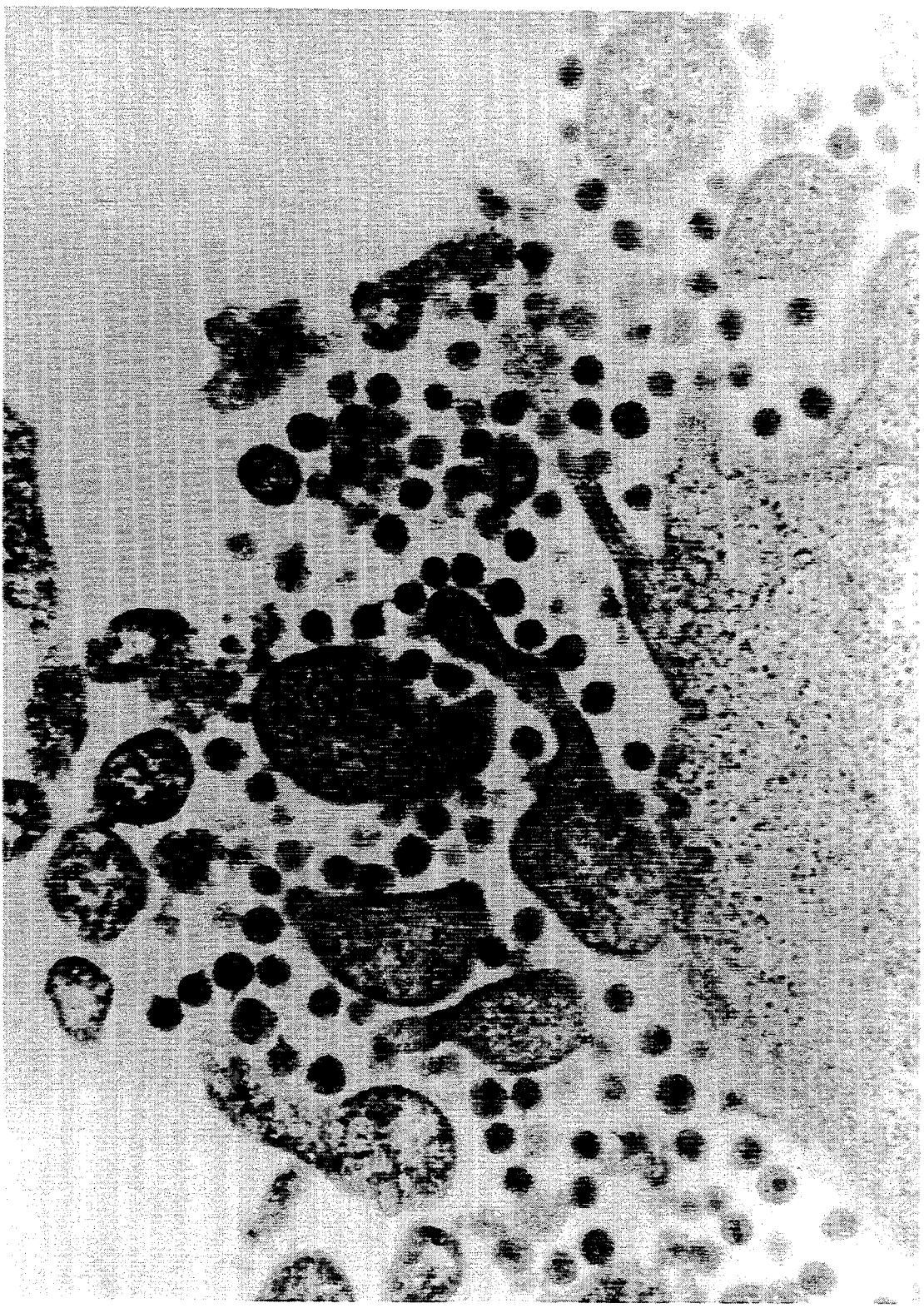
FIG. 5A-5B illustrates electron micrographs of the effect of incubation with the peptides of the invention on the structure of HIV-1.
Figure 5B:
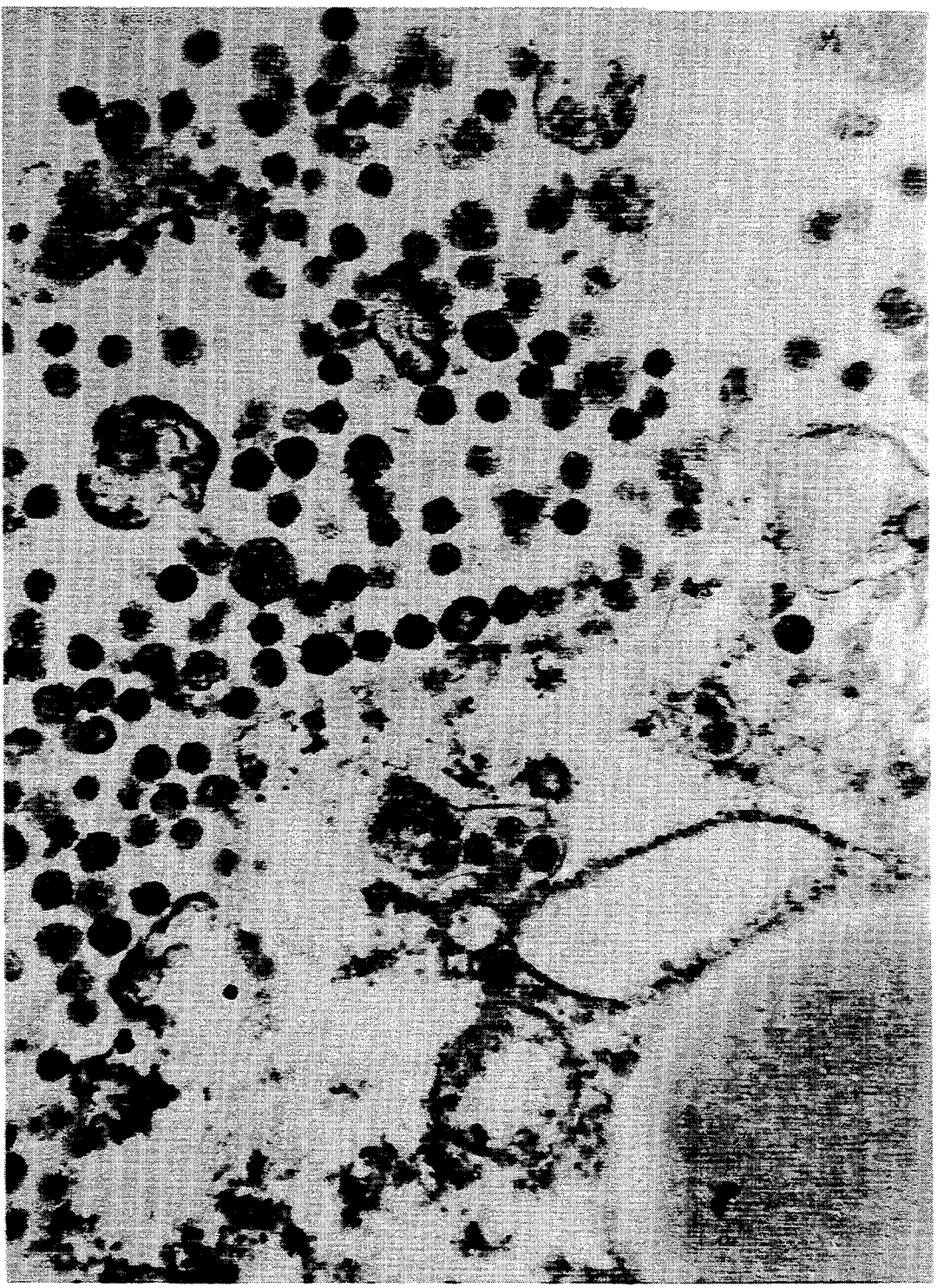

Electron micrographs of HIV-1 virus incubated in the presence or absence of CPF(DD) are shown in FIG. 5A and 5B. FIG. 5A shows an electron micrograph of HIV-1 virus incubated without the addition of CPF(DD) peptides. The virus present display no morphological or other abnormalities. This result is in contrast with virus incubated in the presence of CPF(DD). These results are shown in FIG. 5B. In FIG. 5B many viruses having abnormal morphology are seen; these viruses have been circled in the Figure. This morphological evidence of CPF(DD)-mediated disruption in the structure of the virus is consistent with the biological evidence presented above that CPF(DD) is capable of disrupting the function of HIV-1 virus in vitro, and suggests that the virus can be destroyed in a variety of important biological samples including but not limited to blood, plasma, and semen, by incubation with an effective amount of CPF(DD) and other peptides provided by the present invention.

EXAMPLE 4

HIV-1 Inhibition of MHC-Dependent conjugate Formation Is Overcome by Incubation with CPF Peptides The physiological ligands of CD4 are the Class II major histocompatibility complex (MHC) proteins. This interaction is well known to promote conjugate formation in vitro between human CD4-expressing murine T cell hybridomas and human Class II MHC-expressing cells. Conjugate formation with human Class II MHC-expressing cells can also be observed using the HSBCD4-M.23 cells of Example 2. gp120 is known to inhibit conjugate formation in vitro. Incubation of gp120 or cells with CPF peptides was shown to reverse this gp120-mediated inhibition of MHC-dependent conjugate formation.

Conjugate formation was assayed using HBSCD4-M.23 cells and cells from the human MHC-expressing cell line Daudi (available from ATCC). The HBSCD4-M.23 cells were labeled with 0.5 μg/ml sulfofluorescein diacetate (Molecular Probes, Eugene, Oreg.) and the Daudi cells were labeled with 40 ng/ml hydroethidine (Polysciences, Warrington, Pa.) and mixed at a 1:2 ratio (HBSCD4-M.23:Daudi) at a total concentration of $1\times10^6$ cells/mi. Cells were then incubated in 30 μl RPMI 1640 media at 37° C. for at least 90 minutes in the presence or absence of CPF(DD) or CPF(δF) (at concentrations of 100 μg/ml) and gp120 (20 μg/ml). At the end of the incubation, the cells were gently resuspended to preserve conjugates and scored by fluorescence microscopy. Positive conjugates were scored as at least two cells displaying one fluorescent color bound to at least one cell displaying the other fluorescent color. Samples were analyzed blinded as to their identity, and in duplicate, and at least three counts of 100 fluorescein-labeled cells were performed for each sample. The percentage of conjugates scored was calculated as the total number of conjugates scored divided by the total number of conjugates plus free CD4-expressing (fluorescein-labeled) cells.

The results of this experiment are shown in FIG. 6. As can be seen in the Figure, the addition of gp120 to the cell mixture inhibits the formation of conjugates by more than 50% (lane labeled gp120). Incubation of cells with CPF(DD) alone has essentially no effect on conjugate formation [lane labeled CPF(DD)]. Preincubation of gp120 with CPF(DD) completely restores conjugate formation [lane labeled gp120+CPF(DD)]. Preincubation of gp120 with CPF(δF), on the other hand, does not restrict gp120-mediated inhibition of conjugate formation [lane labeled gp120+CPF(δF)]. These results demonstrate that CPF peptides have no effect adverse on MHC-mediated immune recognition phenomenon, and that incubation of gp120 with these peptides can reverse the gp120-mediated inhibition of this physiological process in vitro. These results suggest that CPF peptides, in a pharmaceutically acceptable carrier, may also be useful for the treatment of HIV-related immunosuppression in humans infected with this virus.

EXAMPLE 5

HIV-1 Inhibition of MHC-Dependent Interleukin-2 Production Is Overcome by Incubation with CFF Peptides A physiological consequence of MHC-dependent immune recognition by CD4-expressing T cells is the production of the lymphokine interleukin 2 (IL-2). gp120 has been shown in vitro to inhibit IL-2 production in stimulated T cells that express CD4. Incubation of gp120 or cells with CPF peptides was shown to reverse this gp120-meditated inhibition of MHC-dependent IL-2 production.

gp120 (at concentrations between 5-10 μg/ml) was incubated for 1 hour at 37° C. in the presence or absence of CPF(DD) or CPF(δF) at concentrations of 200 μg/ml. These gp120 solutions were then diluted 20-fold with PBS and the gp120 reconcentrated by ultrafiltration as described in Example 2. The recovered gp120 solutions were then combined with $1\times10^5$ 16CD4-9 T cell hybridoma cells (available from ATCC) and $2\times10^5$ Daudi cells and cultured overnight at 37° C. IL-2 was detected in the culture supernatants using a cell proliferation assay [Watson, J. Exp. Med. 150: 1510–1515 (1979)], with the modification that proliferation was detected colorimetrically as the cleavage of 3-(4,5- dimethyl-thiazol)-2,6-diphenyl-tetrazolium bromide (MTT) [Finberg et al., Science 249: 287–291 (1990)].

Figure 7:
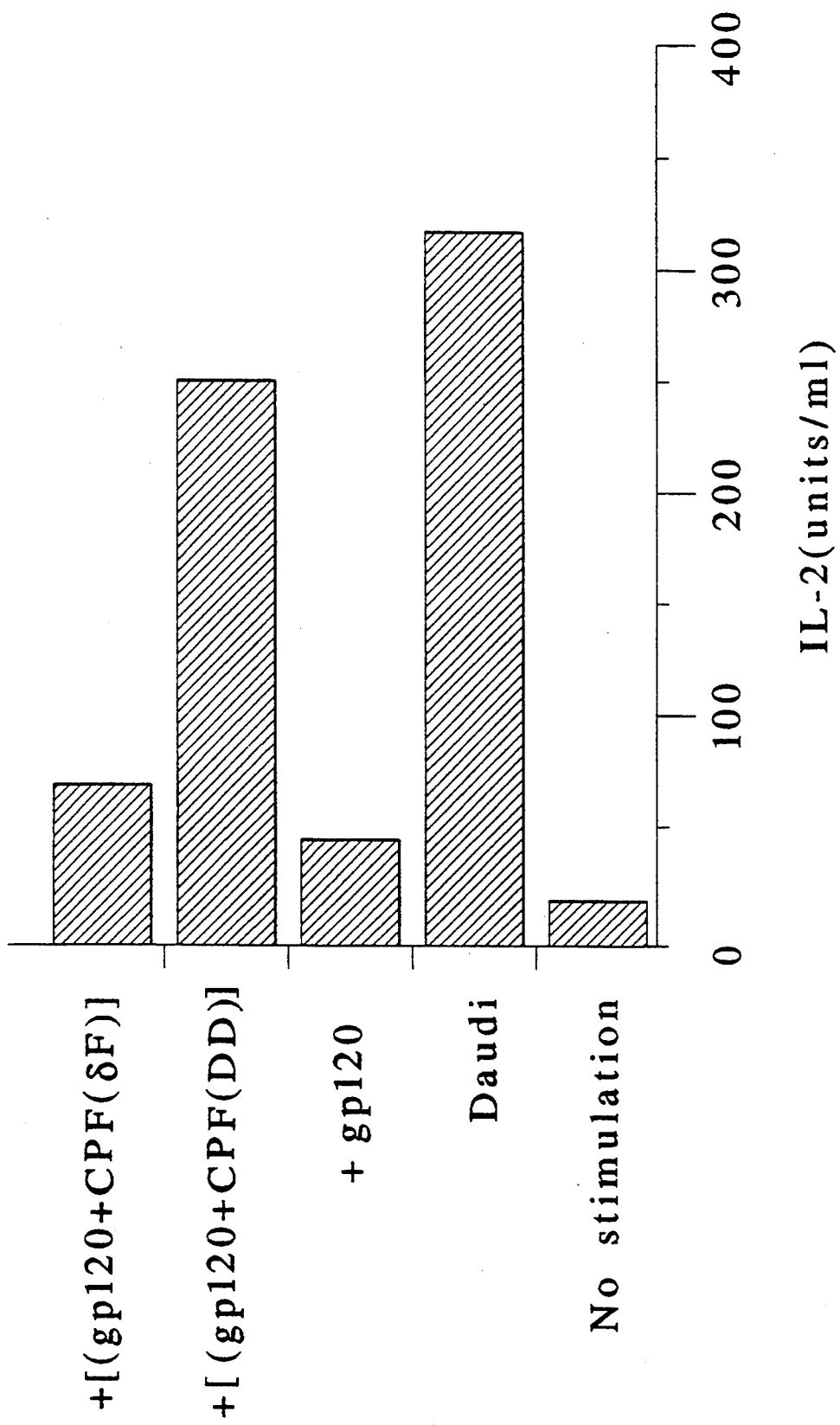
FIG. 7 illustrates the ability of incubation with the peptides of the invention to overcome HIV-1 gp120 mediated inhibition of interleukin 2 production by stimulated T lymphocytes in vitro.

The results of these experiments are shown in FIG. 7. The amount of IL-2 detected is expressed in units/ml with reference to cell proliferation assays performed as described above using known amounts of recombinant IL-2 (rIL-2; Collaborative Research). The T cell hybridoma cells produce little IL-2 in the absence of MHC-dependent stimulation (lane labeled No stimulation). Co-cultivation of 16CD4–9 T cell hybridoma cells with Daudi cells results in the MHC-stimulated production of 300 units/ml IL-2 (lane labeled Daudi). The addition of gp120 to the cultures decreases the amount of IL-2 produced more than 6-fold (lane labeled gp120). Preincubation of gp120 with CPF(DD) almost completely restores IL-2 production in the 16CD4–9 T cell hybridoma cells stimulated by co-cultivation with the Daudi cells [lane labeled gp120+CPF(DD)]. Preincubation of gp120 with CPF(δF) results in a slight increase in the amount of IL-2 produced by these cells [lane labeled gp120 +CPF(δF)]. These results demonstrate that CPF peptides can reverse the gp120-dependent inhibition of IL-2 in stimulated T cells in vitro, and can thereby restore the physiological response of these cells to immune stimulation. These results further suggest that CPF peptides, in a pharmaceutically acceptable carrier, may also be useful for the treatment of HIV-related immunosuppression in humans infected with this virus.

We claim:

1. A method of inhibiting human immunodeficiency virus-1 infection of human cells in vitro comprising contacting such cells with a terminally blocked peptide of formula:

$$A\text{-}[X_n\text{-}]Pro\text{-}Y\text{-}(Leu)_d\text{-}[Z_m\text{-}]B$$

wherein
d = 0 or 1;
A = N-carbomethoxycarbonyl;
B = methyl ester or benzyl ester;
Y = alanine or phenylalanine;
wherein the amino acids are each individually in either the D or L stereochemical configuration and wherein the peptide has anti-HIV-1 properties.

2. The method according to claim 1 wherein the proline is in the D stereochemical configuration.

3. The method according to claim 1 wherein the Y amino acid is in the D stereochemical configuration.

4. The method according to claim 1 wherein both the proline and the Y amino acids are in the D stereochemical configuration.

5. The method according to claim 1 wherein Y is alanine.

6. The method according to claim 1 wherein Y is phenylalanine.

7. The method according to claim 1 wherein the peptide is N-carbomethoxycarbonyl-prolyl-phenylalanyl-benzyl ester and wherein the amino acids are each individually in either the D or L stereochemical configuration.

8. The method according to claim 1 wherein the peptide is N-carbomethoxycarbonyl-prolyl-phenylalanyl-methyl ester and wherein the amino acids are each individually in either the D or L stereochemical configuration.

9. The method according to claim 1 wherein the peptide is N-carbomethoxycarbonyl-prolyl-alanyl-benzyl ester and wherein the amino acids are each individually in either the D or L stereochemical configuration.

10. The method according to claim 1 wherein the peptide is N-carbomethoxycarbonyl-prolyl-alanyl-methyl ester and wherein the amino acids are each individually in either the D or L stereochemical configuration.

11. The method according to claim 1 wherein the peptide is N-carbomethoxycarbonyl-prolyl-phenylalanyl-leucyl-benzyl ester and wherein the amino acids are each individually in either the D or L stereochemical configuration.

12. The method according to claim 1 wherein the peptide is N-carbomethoxycarbonyl-prolyl-alanyl-leucyl-benzyl ester and wherein the amino acids are each individually in either the D or L stereochemical configuration.

13. A method according to claim 1 wherein the human cells are hematopoietic cells.

14. A method according to claim 1 wherein the human cells are T lymphocytes.

15. A pharmaceutically acceptable composition effective according to the method of claim 1 comprising an effective amount of the terminally blocked peptide of formula:

$$A\text{-}Pro\text{-}Y\text{-}(Leu)_d\text{-}B$$

wherein
d = 0 or 1:
A = N-carbomethoxycarbonyl:
B = methyl ester or benzyl ester;
Y = alanine or phenylalanine:
wherein the amino acids are each individually in either the D or L stereochemical configuration and wherein the peptide has anti-HIV-1 properties, and a pharmaceutically acceptable carrier or diluent.

16. A method of essentially inactivating human immunodeficiency virus-1 in vitro comprising contacting a mixture of such virus with a terminally-blocked peptide of formula:

$$A\text{-}Pro\text{-}Y\text{-}(Leu)d\text{-}B$$

wherein d = 0 or 1;
A = N-carbomethoxycarbonyl;
B = methyl ester or benzyl ester:
Y = alanine or phenylalanine;
wherein the amino acids are each individually in either the D or L stereochemical configuration and wherein the peptide has anti-HIV-1 properties.

17. The method of claim 1 wherein the human cells are contacted with a mixture of the peptide of claim 1 and an effective amount of a second antiviral compound in a pharmaceutically acceptable carder.

18. The method of claim 17 wherein the second antiviral compound is azidothymidine.

19. A method for diagnosing human immunodeficiency virus-1 infection in an animal, the method comprising the following steps:
    (a) providing a first mixture comprised of a terminally-blocked peptide of formula:

$$A\text{-}Pro\text{-}Y\text{-}(Leu)_d\text{-}B$$

wherein d = 0 or 1;
A = N-Carbomethoxycarbonyl;
B = methyl ester or benzyl ester;
Y = alanine or phenylalanine;

wherein the amino acids are each individually in either the D or L stereochemical configuration, a second mixture comprised of a standard amount of gp120 protein of HIV-1, and a third mixture comprised of a diagnostically-significant tissue sample or bodily fluid;
  (b) providing a specific binding reaction mixture by contacting the first, second and third provided mixtures;
  (c) incubating the reaction mixture for a time sufficient to allow binding between the peptide and the viral protein present in the second provided mixture and the third provided mixture;

(d) detecting the extent of the binding reaction by determining the amount of the standard viral protein bound to the peptide; and (e) determining the extent of viral infection by comparing the amount of binding of the standard viral protein to the peptide in the presence of the tissue sample or bodily fluid of the third provided mixture with the amount of binding of the standard viral protein to the peptide in the absence of the tissue sample or bodily fluid of the third provided mixture.

20. A method according to claim 19 wherein the animal is a human.

21. The method of claim 1 wherein the human cells are contained in human blood or blood products derived therefrom.

22. The method of claim 16 wherein the virus is contained in human blood or blood products derived therefrom.

23. The method of claim 17 wherein the human cells are contained in human blood or blood products derived therefrom.

* * * * *

UNITED STATES PATENT AND TRADEMARK OFFICE
CERTIFICATE OF CORRECTION

PATENT NO. : 5,447,915
DATED : September 5, 1995
INVENTOR(S) : Stuart Schreiber, et al It is certified that error appears in the above-identified patent and that said Letters Patent is hereby corrected as shown below:

At column 2, line 55, change "BJorck" to --Bjorck--
At column 2, line 63, change "Sendal" to --Sendai--
At column 5, line 25, change "vicro" to --vitro--
At column 5, line 47, change the formula: "$A\text{-}X_n\text{-}Pro\text{-}Y\text{-}(Leu)_d\text{-}Z_m\text{-}E$" to --$A\text{-}X_n\text{-}Pro\text{-}Y\text{-}(Leu)_d\text{-}Z_m\text{-}B$--
At column 7, line 19, change "hamatopoietic" to --hematopoietic--
At column 9, line 9, change "vital" to --viral"
At column 9, line 28, change "in vicro" to --in vitro--
At column 10, line 18, change "SemItki Forest virus" to --Semliki Forest virus--
At column 11, line 49, change "provided By the invention" to --provided by the invention--
At column 12, line 28, change "1:1 acetone:-water" to --1:1 acetone:water--
At column 12, line 38, change "1.99 E of a clear" to --1.99 g of a clear--
At column 13, line 33, change "sufficient to achieve &" to --sufficient to achieve a--
At column 13, lines 55-56, change "1:1 hexanes-:ethyl acetate" to --1:1 hexanes:ethyl acetate--
At column 14, line 10, change "triethylamine (0,794 ml, 5.7 mmol)" to --triethylamine (0.794 ml, 5.7 mmol)--
At column 15, lines 23-24, change "transfaction" to --transfection--
At column 15, line 41, change "FatScan" to --FACScan--
At column 15, line 68, change "[CPF(F→a)]" to --[CPF(F→A)]--
At column 16, lines 8 and 9, change "[CPF(N    Boc)]" should not be separated by a line, reading instead --[CPF(N-Boc)]--

UNITED STATES PATENT AND TRADEMARK OFFICE
CERTIFICATE OF CORRECTION

PATENT NO. : 5,447,915
DATED : September 5, 1995
INVENTOR(S) : Stuart Schreiber, et al It is certified that error appears in the above-identified patent and that said Letters Patent is hereby corrected as shown below:

At column 17, line 32, change "Inbibition" to --Inhibition--
At column 17, line 40, change "supernatants of lo virally-infected" to --supernatants of virally infected--
At column 17, line 42, change "[Finberg ecal.," to --[Finberg et al.,--
At column 18, line 33, change "(OKTS, obtained from ATCC)" to --(OKT8, obtained from ATCC)--
At column 18, line 39, change "or with CPF(6F)" to --or with CPF($\delta$F)--
At column 18, line 55, change "concentrations of 80 g/ml and above" to --concentrations of 80 µg/ml and above--
At column 18, line 58, change "effect of CFF peptides" to --effect of CPF peptides--
At column 19, line 4, change "after 2, $\propto$ and 6 days" to --after 2, 4 and 6 days--
At column 20, line 6, change "1 × $10^6$ cells/mi." to --1 × $10^6$ cells/ml.--
At column 20, line 45, change "Incubation with CFF" to --Incubation with CPF--

In claim 1, column 27, line 23 change "d=0or 1;" to --d=0 or 1;--
In claim 15, column 28, line 29, change "d=0or 1:" to --d=0 or 1;--
In claim 15, column 28, line 30, change "A=N-carbomethoxycarbonyl:" to --"A=N-carbomethoxycarbonyl;--
In claim 15, column 28, line 32, change "Y=alanine or phenylalanine:" to --Y=alanine or phenylalanine;--
In claim 16, column 28, line 42, change the formula "A-Pro-Y-(Leu)d-B" to --A-Pro-Y-(Leu)$_d$- as in the amendment to the pending claim (number 28), filed March 30, 1994.

UNITED STATES PATENT AND TRADEMARK OFFICE
CERTIFICATE OF CORRECTION

PATENT NO. : 5,447,915
DATED : September 5, 1995
INVENTOR(S) : Stuart Schreiber, et al It is certified that error appears in the above-identified patent and that said Letters Patent is hereby corrected as shown below:

At column 3, line 49, change "Fischer, et al.," to --Fischer et al.,--
At column 7, line 25, change "comprised of an therapeutically effective amount" to --comprised of a therapeutically effective amount--
At column 15, line 25, change "Natl. Acad. Sci. 87: xxxx (1990)" to --Natl. Acad. Sci. 87: 5001-5005 (1990)--
At column 15, line 27, change "gp 120" to --gp120--
At column 15, line 38, change "propidium iodine" to --propidium iodide--
At column 15, line 47, change "gp 120" to --gp120--
At column 17, lines 36-37, change "Accession No. CRL 8543) human immunodeficiency virus" to --Accession No. CRL 8543) with human immunodeficiency virus--
At column 18, line 47, change "FIG 3C, indicate that" to --FIG 3C, indicating that--

In claim 1, column 27, line 20, change the formula "A-[$X_n$-]Pro-Y-(Leu)$_d$-[$Z_m$-]B" to --A-[$X_n$]-Pro-Y-(Leu)$_d$-[$Z_m$]-B--

Signed and Sealed this

Sixth Day of July, 1999

Attest:

Q. TODD DICKINSON

*Attesting Officer*    Acting Commissioner of Patents and Trademarks